(12) United States Patent
Lian

(10) Patent No.: US 9,539,044 B2
(45) Date of Patent: Jan. 10, 2017

(54) SYSTEMS AND INSTRUMENTALITIES FOR USE IN REMOVAL OF TIBIAL PROSTHESES OF TOTAL ANKLE REPLACEMENTS

(71) Applicant: George John Lian, Sacramento, CA (US)

(72) Inventor: George John Lian, Sacramento, CA (US)

(73) Assignee: George John Lian, Sacramento, CA (US)

( * ) Notice: Subject to any disclaimer, the term of this patent is extended or adjusted under 35 U.S.C. 154(b) by 511 days.

(21) Appl. No.: 13/573,887

(22) Filed: Oct. 12, 2012

(65) Prior Publication Data

US 2013/0046313 A1 Feb. 21, 2013

Related U.S. Application Data

(63) Continuation-in-part of application No. 13/068,290, filed on May 6, 2011, now Pat. No. 8,475,463, and a continuation-in-part of application No. 12/798,417, filed on Apr. 2, 2010, now Pat. No. 8,337,503, said application No. 13/068,290 is a continuation-in-part of application No. 12/798,417.

(60) Provisional application No. 61/627,491, filed on Oct. 14, 2011, provisional application No. 61/648,260, filed on May 17, 2012, provisional application No. 61/212,533, filed on Apr. 13, 2009, provisional application No. 61/270,203, filed on Jul. 6, 2009.

(51) Int. Cl.
| | |
|---|---|
| A61B 17/92 | (2006.01) |
| A61F 2/46 | (2006.01) |
| A61F 2/92 | (2013.01) |
| A61B 17/16 | (2006.01) |
| A61B 17/17 | (2006.01) |

(52) U.S. Cl.
CPC .......... *A61B 17/92* (2013.01); *A61B 17/1682* (2013.01); *A61B 17/1739* (2013.01); *A61F 2/46* (2013.01); *A61F 2/4606* (2013.01); *A61F 2/92* (2013.01); *A61B 17/921* (2013.01); *A61B 2017/1775* (2013.01)

(58) Field of Classification Search
USPC ............. 606/86 R, 87, 99; 623/21.18, 47–52
See application file for complete search history.

(56) References Cited

U.S. PATENT DOCUMENTS

2010/0057216 A1* 3/2010 Gannoe et al. ............ 623/21.18

\* cited by examiner

*Primary Examiner* — Nicholas Woodall
(74) *Attorney, Agent, or Firm* — Dennis A. DeBoo; Audrey A. Millemann; Weintraub Tobin

(57) ABSTRACT

A system comprising instrumentalities and methods for removing intramedullary stem component pieces of a tibial implant from a distal tibia.

19 Claims, 13 Drawing Sheets

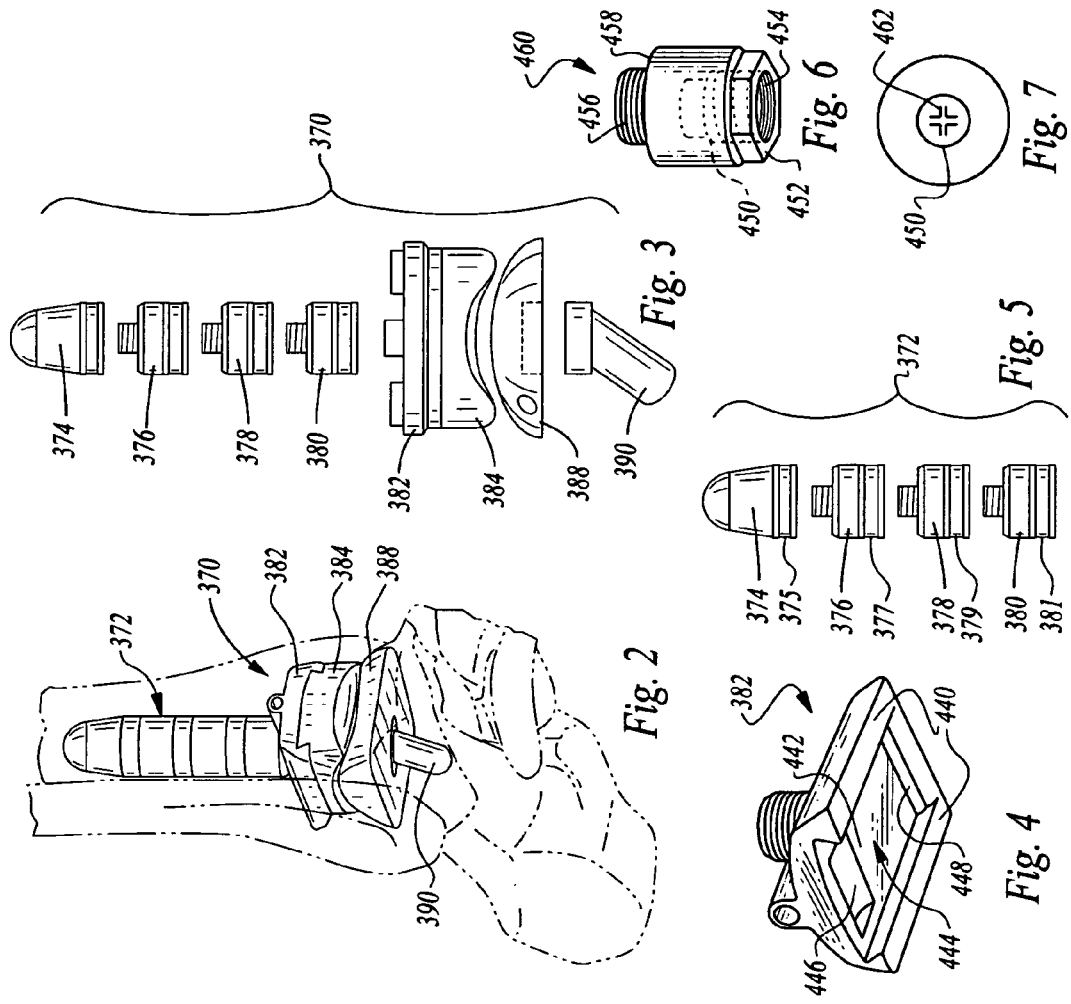

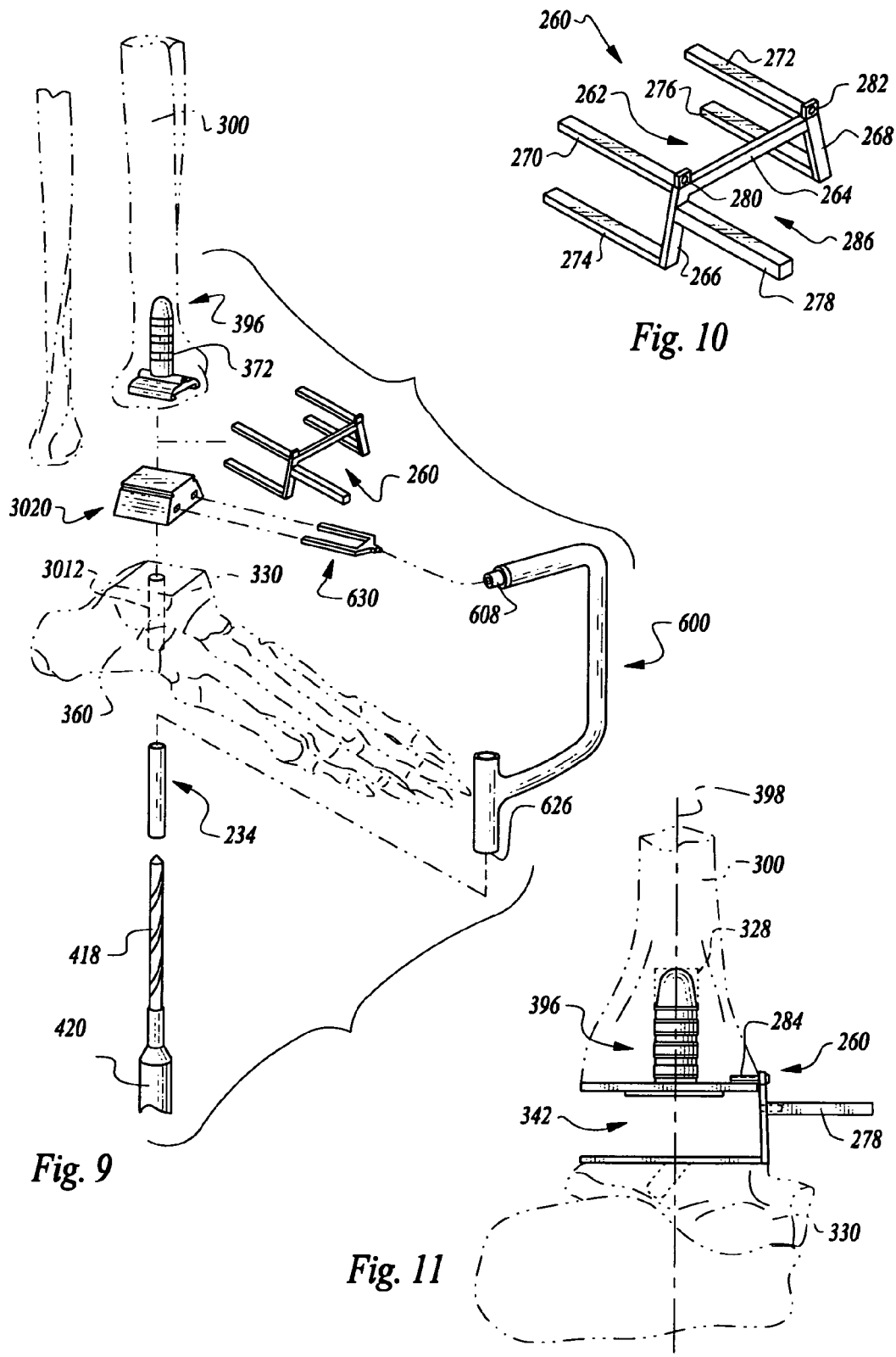

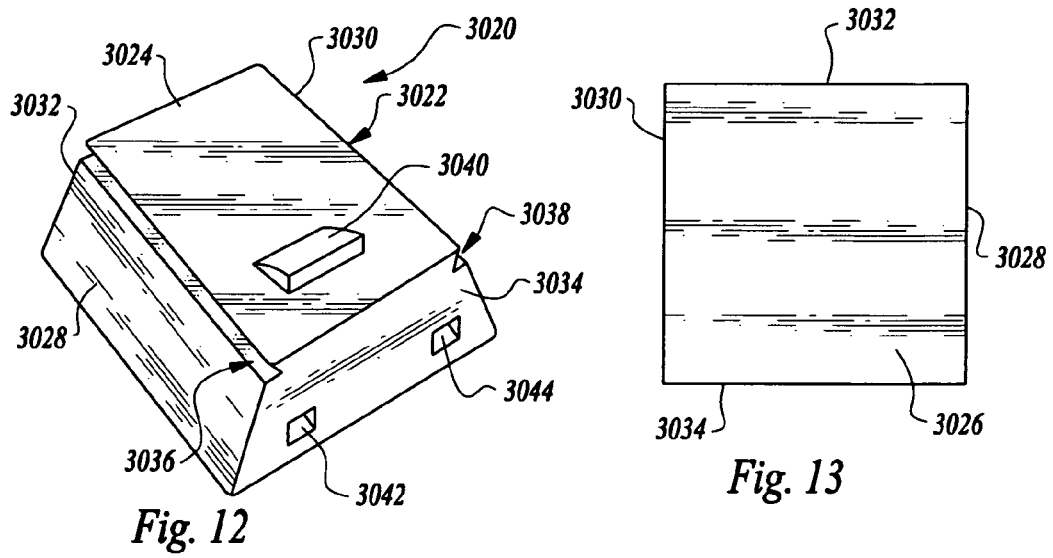
Fig. 12
Fig. 13
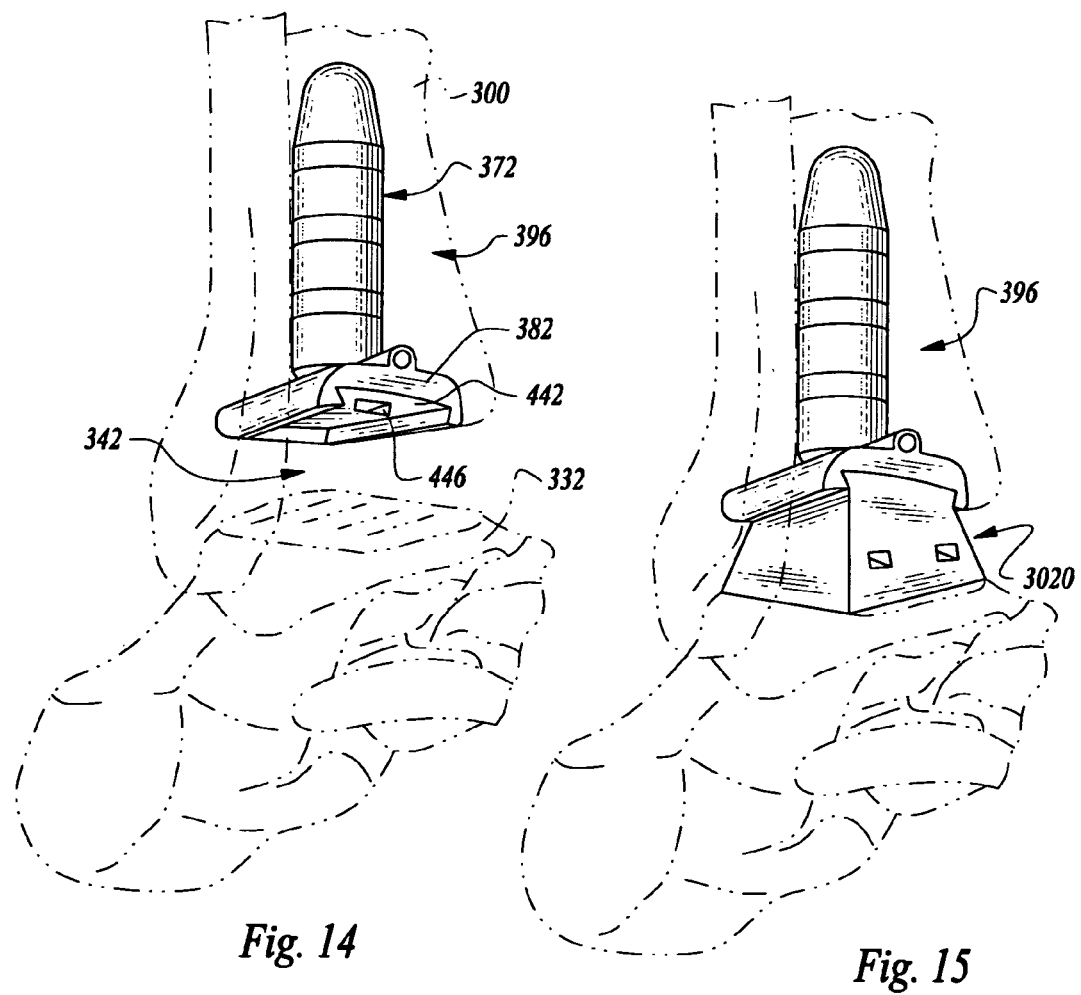
Fig. 14
Fig. 15

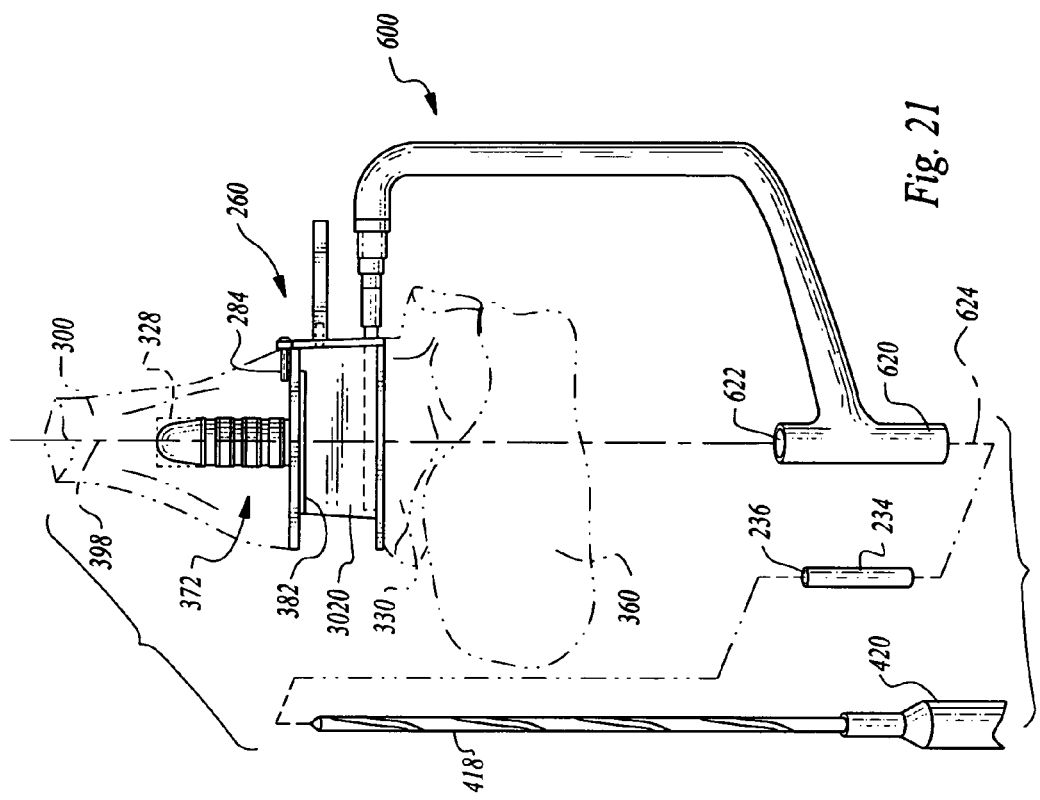
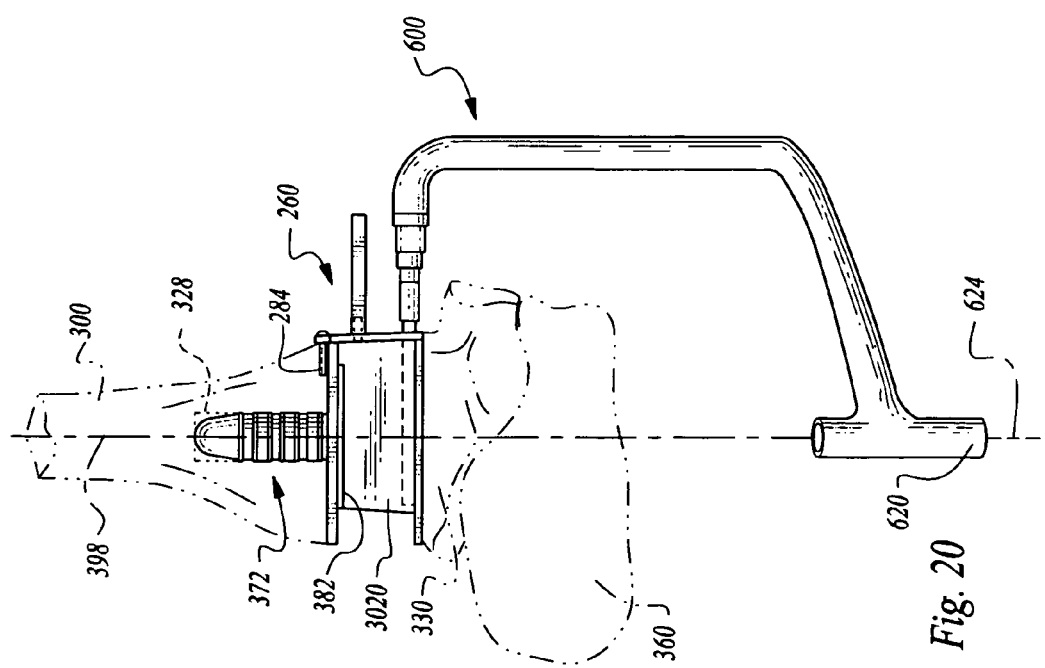

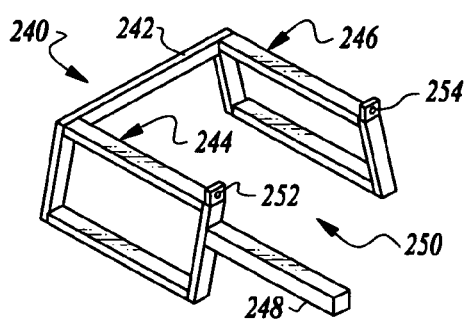
Fig. 24
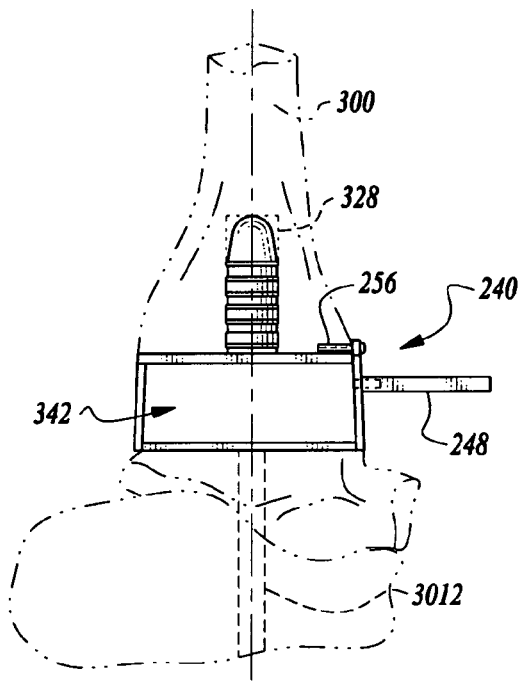
Fig. 25
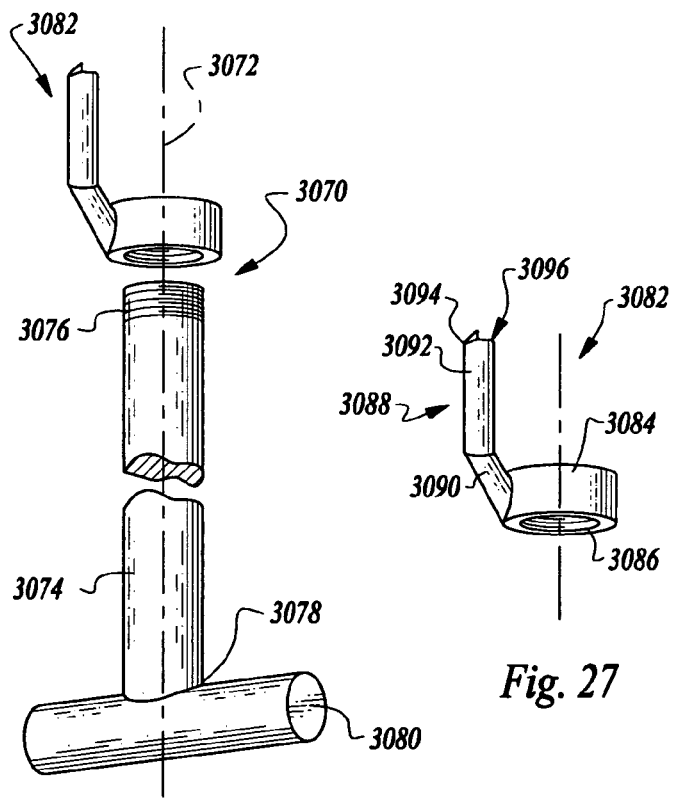
Fig. 26
Fig. 27
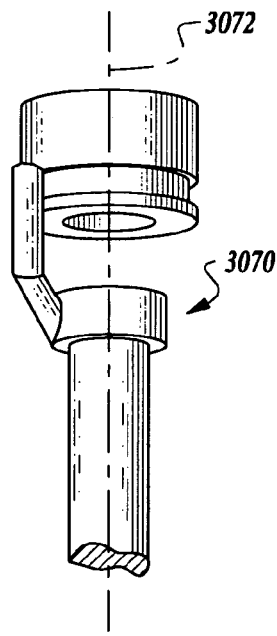
Fig. 28

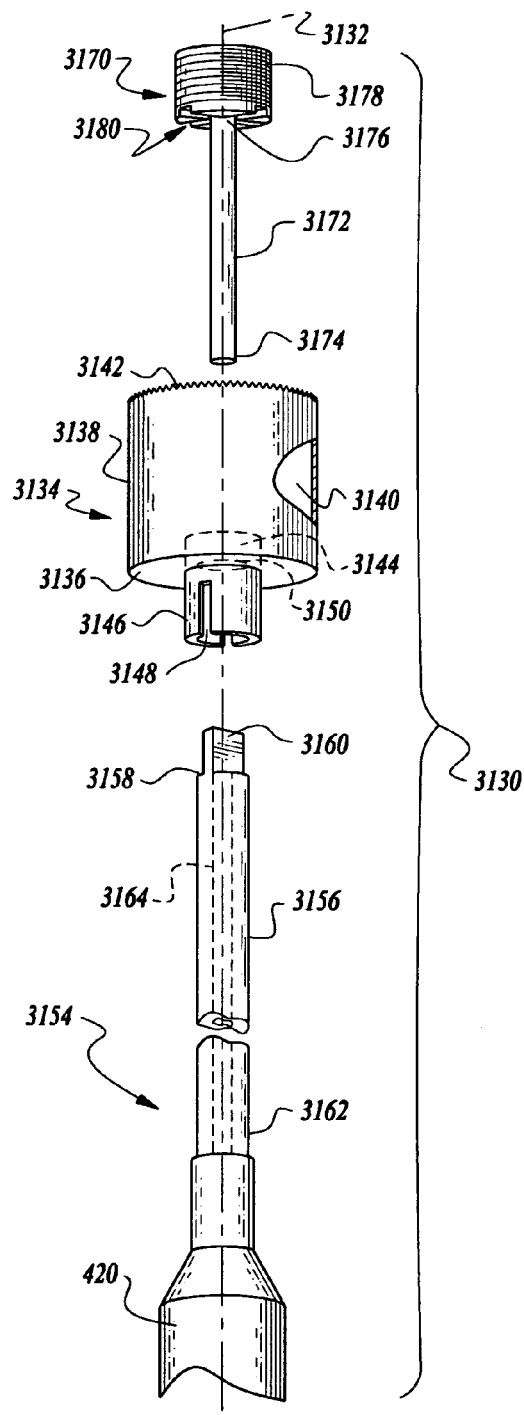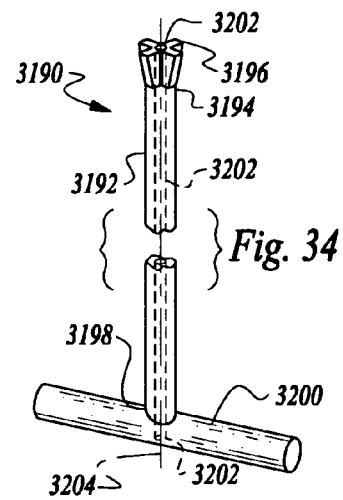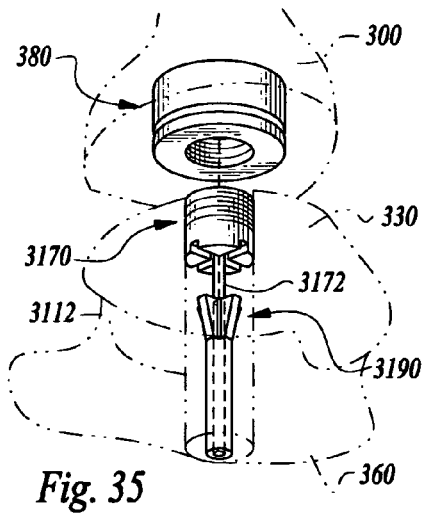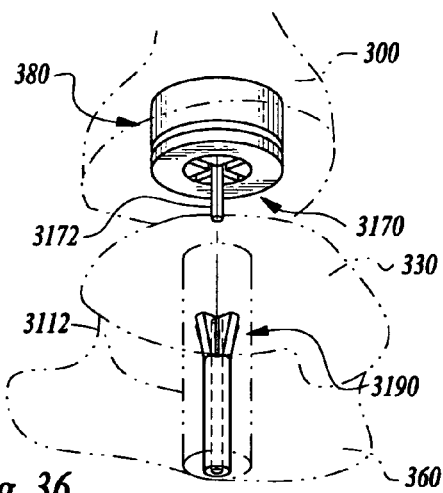
Fig. 33
Fig. 34
Fig. 35
Fig. 36

SYSTEMS AND INSTRUMENTALITIES FOR USE IN REMOVAL OF TIBIAL PROSTHESES OF TOTAL ANKLE REPLACEMENTS

CROSS-REFERENCE TO RELATED APPLICATIONS

This application claims priority under 35 USC Section 119(e) to U.S. Provisional Patent Application No. 61/627,491, filed Oct. 14, 2011 and also to U.S. Provisional Patent Application No. 61/648,260 filed May 17, 2012, both disclosures of which are incorporated herein by reference in their entireties.

This application is a continuation-in-part patent application of U.S. patent application Ser. No. 13/068,290, filed May 6, 2011, currently pending, and also this application and U.S. patent application Ser. No. 13/068,290 are both continuation-in-part patent applications of U.S. patent application Ser. No. 12/798,417, filed Apr. 2, 2010, currently pending and which claims priority under 35 USC Section 119(e) to U.S. Provisional Patent Application No. 61/212,533, filed Apr. 13, 2009 and to U.S. Provisional Application No. 61/270,203, filed Jul. 6, 2009, all four disclosures of which are incorporated herein by reference in their entireties.

FIELD OF THE INVENTION

This invention relates generally to systems and instrumentalities for use in removal of tibial prostheses of total ankle replacements, and, in particular, to systems and instrumentalities for removing a tibial prosthesis having an intramedullary stem.

BACKGROUND OF THE INVENTION

Generally, there are several designs of total ankle replacement prostheses. One type of total ankle replacement prostheses comprises a tibial implant with an elongated intramedullary stem. This type of prosthesis is exemplified by a total ankle replacement prostheses sold by Wright Medical Technology, Inc. (5677 Airline Road, Arlington, Tenn. 38002, USA) under the trademark INBONE Total Ankle System. In this system, the total ankle replacement prostheses is comprised of a tibial implant having an elongated intramedullary stem formed by a plurality of modular stem component pieces, a talar implant, and a polyethylene spacer.

Generally, this system has five sizes of implant sets that are employed as a function of the size of the ankle bones of a particular patient. Additionally, the tibial implant is constructed from different stem component pieces. The inferior part is a tibial tray. This has a set size and morphology specified by the size of the implant set chosen. Superior to this is a base, which also has a set size and morphology specified by the size of the implant set chosen. Superior to this are a variable number and size of stem component pieces that are chosen by the surgeon during the procedure to give the best fit in the tibial intramedullary canal. Furthermore, the talar implant has a set size and morphology specified by the size of the implant set chosen. There is a stem that fits into the inferior portion of the talar implant and extends inferiorly either 10 mm or 14 mm at a defined angle. The choice of which stem length to use is made by the surgeon during the procedure. Moreover, each implant set has a defined number of polyethylene spacers of varying height that fit into the tibial tray on the tibial implant. The height of the spacer to be used is chosen by the surgeon during the procedure, after the tibial and talar implant have been fit into the bones.

During the surgical procedure, the elongated intramedullary stem is constructed by coupling together the plurality of modular stem component pieces through an anterior ankle opening in a space formed between the lower end of the tibia and the upper end of the talus. This construction is performed after bone cuts have been made in those two bones, and the cut sections of bone have been removed to form the space. A second opening in the skin is made on the bottom of the heel, and a channel is drilled up through this skin incision, and then further up through the calcaneus and talus bones. That channel allows passage of instruments that aid in coupling the modular stem component pieces together to form the elongated intramedullary stem of the tibial prosthesis at a desired location in the tibia. The combination of these modular component pieces to form the tibial implant requires an intramedullary approach to the distal tibia.

There is a need to overcome the significant shortcomings in the removal of total ankle replacement prostheses such as the total ankle replacement prostheses delineated above during revision surgical procedures. In particular, there is a need to overcome the significant shortcomings in the removal of the elongated intramedullary stem of the tibial implant from the distal tibia during revision surgical procedures.

Of particular concern in the existing techniques for the removal of the tibial implant is the requirement for large bone windows to be cut into the lower end of the tibia to remove the elongated intramedullary stem component pieces of the tibial implant that have become fixed into the bone during the initial surgical procedures. The result of this bone destruction yields a tibia that makes further reconstructive procedures particularly problematic.

Accordingly, there is a particular need to overcome the significant shortcomings in the removal of the elongated intramedullary stem component pieces of the tibial implant from the distal tibia during revision surgical procedures.

BRIEF SUMMARY OF THE INVENTION

Accordingly, and in one aspect, an embodiment of the invention ameliorates or overcomes one or more of the significant shortcomings of the known prior art by providing a system: instruments and methods for removing intramedullary stem component pieces of a tibial implant from a distal tibia without the requirement for large bone windows to be cut into the lower end of the tibia to remove the intramedullary stem component pieces of the tibial implant for conserving the bone of the distal tibia.

In one aspect, an embodiment of the invention provides a tibial prosthesis removal system: instruments and methods for removing intramedullary stem component pieces of a tibial implant from a distal tibia by forming a channel or passageway through a calcaneus and talus that is aligned with the longitudinal axis of the modular tibial stem component implant even if the modular tibial stem component implant has shifted into a slight angulation off the alignment of the original insertion axis; stabilizing the ankle, foot, and leg of the patient with the modular tibial stem component implant; circumferentially cutting tibia bone circumscribing an inferior most stem component piece of the modular tibial stem component implant by utilizing the aligned channel; unscrewing the inferior most stem piece by utilizing the aligned channel; grasping and removing the unscrewed inferior most stem piece by utilizing the aligned channel, determining if further stem component pieces remain implanted; and repeating the circumferentially cutting, unscrewing, and grasping and removing steps until all implanted stem component pieces have been removed.

Accordingly, it should be apparent that numerous modifications and adaptations may be resorted to without departing from the scope and fair meaning of the claims as set forth herein below following the detailed description of the invention.

BRIEF DESCRIPTION OF THE DRAWINGS

FIG. 1 is a general block diagram of an embodiment of a tibial prosthesis removal system.

FIG. 2 is a side and front perspective view of a replacement of a total ankle joint with an embodiment of an ankle prosthesis comprised of a modular tibial or intramedullary stem component, a tibial tray component, a polyethylene spacer or poly insert component, a talar dome component, and a talar stem component.

FIG. 3 is an exploded parts view of the ankle prosthesis illustrated in FIG. 2.

FIG. 4 is a side, front, and bottom perspective view of the tibial tray component illustrated in FIGS. 2 and 3.

FIG. 5 is a side elevational view of the modular tibial or intramedullary stem component illustrated in FIGS. 2 and 3.

FIG. 6 is a side elevational view of one of the modular tibial stem component pieces.

FIG. 7 is a bottom elevational view of the modular tibial stem component piece illustrated in FIG. 6.

FIG. 9 is a fragmentary front and side perspective view of a human leg and further illustrating a front and side perspective view of a tibial prosthesis, an embodiment of a double fork frame, an embodiment of a tibial tray alignment insert, an embodiment of a tuning fork shaped adaptor, an embodiment of a C-shaped outrigger alignment guide, an embodiment of a drill guide, an embodiment of a drill bit, and an embodiment of a fragmented drill for utilization in forming a channel through the calcaneus and the talus of the foot.

FIG. 10 is a side, front, and top perspective view of the double fork frame.

FIG. 11 a side elevational view of the double fork frame positioned in a tibial-talar space, a side elevational view of the modular tibial stem component and tibial tray component forming an in situ tibial prosthesis, and a fragmented view of the tibia, talus, and calcaneus.

FIG. 12 is a side, front, and top perspective view of the tibial tray alignment insert illustrated in FIG. 9.

FIG. 13 is a bottom elevational view of the tibial tray alignment insert illustrated in FIG. 12.

FIG. 14 is a side and front perspective view of the in situ tibial prosthesis and the tibial-talar space, and a fragmentary front and side perspective view of the human leg and foot.

FIG. 15 is a side and front perspective view of the in situ tibial prosthesis and the tibial tray alignment insert configured to fit within the tibial-talar space, and a fragmentary front and side perspective view of the human leg and foot.

FIG. 20 is a side elevational view of the C-shaped outrigger alignment guide operatively coupled to the tuning fork shaped adaptor inserted at least partially into the tibial tray alignment insert which is operatively coupled to the tibial tray, the double fork frame in the tibial-talar space, and the in situ tibial prosthesis, and further illustrating a fragmented view of the tibia, talus, and calcaneus.

FIG. 21 is a side elevational view of the drill bit and drill (fragmented), the drill guide, the C-shaped outrigger alignment guide operatively coupled to the tuning fork shaped adaptor inserted at partially into the tibial tray alignment insert which is operatively coupled to the tibial tray, the double fork frame in the tibial-talar space, and the in situ tibial prosthesis, and further illustrating a fragmented view of the tibia, talus, and calcaneus.

FIG. 24 is a side, front, and top perspective view of an embodiment of a skeleton cage or frame.

FIG. 25 is a side elevational view of the skeleton cage or frame positioned in the tibial-talar space, a side elevational view of the modular tibial stem component, and a fragmented view of the tibia, and a fragmented view of the talus and calcaneus having the channel disposed therethrough wherein the channel has a central long axis coextensive or coincident with the central long axis of the modular tibial stem component.

FIG. 26 is an exploded parts view of an embodiment of a bone cutting means in the form of an embodiment of an offset chisel device comprised of a chisel head portion surmounting one end of an elongated shaft having a handle disposed at an opposing end thereof.

FIG. 27 is a side elevational view of the chisel head portion illustrated in FIG. 26.

FIG. 28 is a side elevational view of an embodiment of a tibial or intramedullary stem component piece, a side elevational view of the chisel head portion having a chisel with a radius of curvature matching or complemental to a radius of an exterior curvature of the tibial or intramedullary stem component piece, and a fragmented view of the elongated shaft coupled to the chisel head portion.

FIG. 33 is an exploded parts view of an embodiment of a combination cylindrical saw and threaded centering device comprised of a cylindrical saw head, a cylindrical saw driver, and a threaded centering device, and further illustrating a fragmented view of a drill operatively coupled to the cylindrical saw driver.

FIG. 34 is a side elevational view of an embodiment of a long handle instrument.

FIG. 35 is a side elevational view of the long handle instrument having an elongated shaft passing through the channel and terminating to a patterned head in the tibial-talar space and in engagement with the threaded centering device, and further illustrating a fragmented view of the tibia, talus, and calcaneus.

FIG. 36 is a side elevational view of the long handle instrument having the elongated shaft passing through the channel and terminating to the patterned head in the tibial-talar space which is disengage from the threaded centering device after threading the threaded centering device into an inferior threaded bore of the most inferiorly located tibial stem component piece, and further illustrating a fragmented view of the tibia, talus, and calcaneus.

DETAILED DESCRIPTION OF THE INVENTION

Introduction

Figure 8:
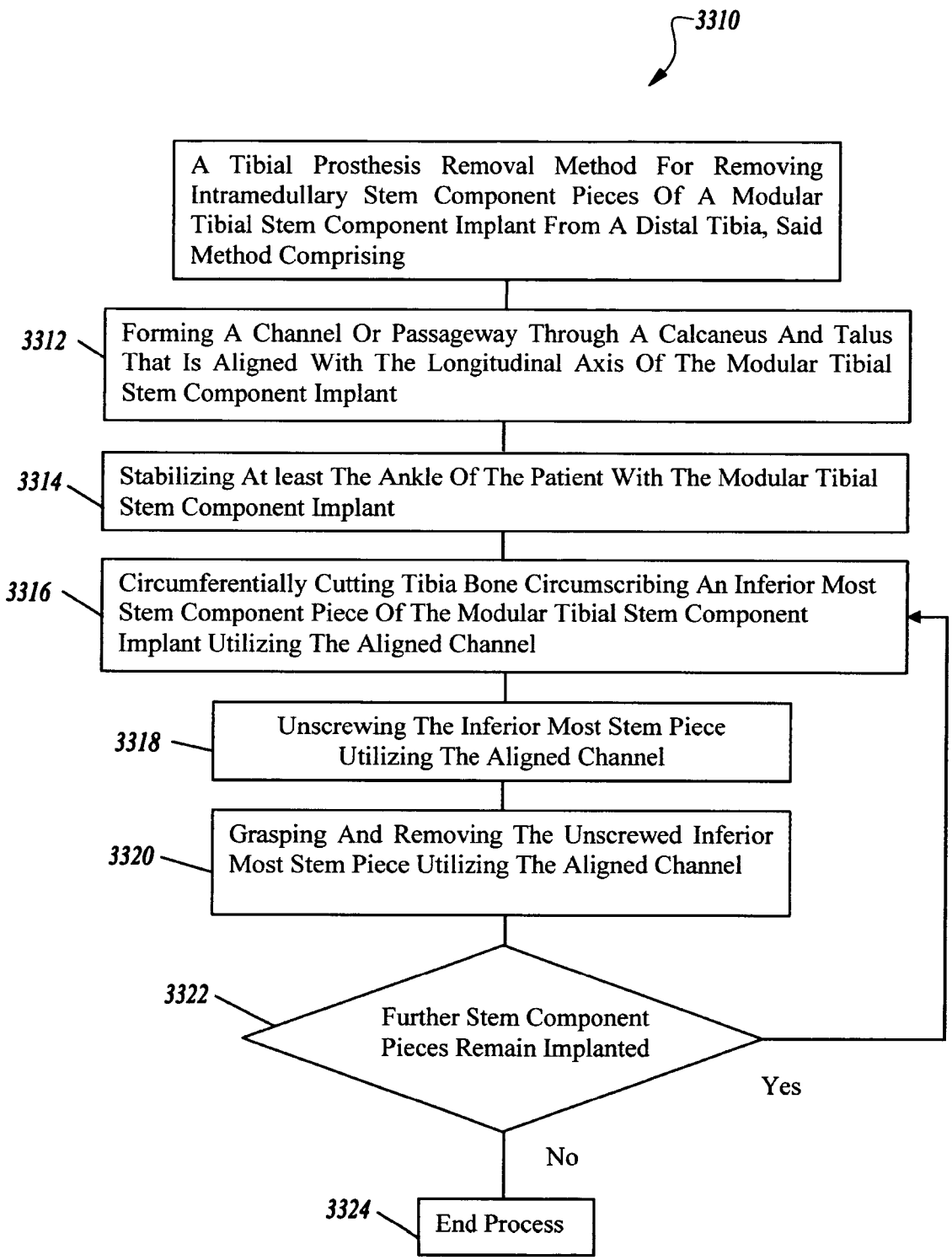
FIG. 8 is a flowchart view of an embodiment of a tibial prosthesis removal method.

Considering the drawings, wherein like reference numerals denote like parts throughout the various drawing figures, reference numeral 3010 is directed to a system for use in removal of a tibial stem of total ankle prosthesis such as, but not limited to, total ankle prosthesis 370.

The total ankle prosthesis 370 is sold by Wright Medical Technology, Inc. (5677 Airline Road, Arlington, Tenn. 38002, USA) under the trademark INBONE Total Ankle System and is presently available in five sizes (number 2, 3, 4, 5, or 6), left and right.

A system for use in the total ankle replacement with the total ankle prosthesis 370 is described in detail in U.S. Patent Application Publication No.: 2010/0262150 and U.S. Patent Application Publication No.: US 2011/0218542, which are both incorporated herein by reference in their entireties as though fully set forth herein and wherein each has the same inventor as the inventor of system 3010.

Total Ankle Prosthesis 370

In one embodiment, and referring to FIGS. 1 and 2, prosthesis 370 is comprised of a modular tibial stem component 372, a tibial tray component 382, a polyethylene or poly insert component 384, a talar dome component 388, and a talar stem component 390.

Talar Stem Component 390

As illustrated in FIGS. 2 and 3, the talar stem component 390 is connected to an inferior side of the talar dome component 388 and extends at a precise angle inferiorly away from the talar dome component 388 and has, in one embodiment, a 10 mm diameter and is available in 10 and 14 mm lengths.

Talar Dome Component 388

The talar dome component 388 includes an upper convex surface that mates with a lower concave surface of the poly insert component 384 that is carried by the tibial tray component 382 to form a complementary ball-and-socket type structure.

Tibial Tray Component 382

As illustrated in FIG. 4, the tibial tray component 382 also comprises oppositely spaced, inwardly tapered side rails 440. The side rails 440 extend in an anterior to posterior direction along the underside 442 of the tibial tray component 382. The tapered side rails 440 form a channel 444 between them. The underside 442 of the tibial tray component 382 includes a shaped depression or notch 446 near its anterior edge wherein the shaped depression or notch 446 is in open communication with the channel 444.

Modular Tibial Stem Component 372

As illustrated in 5, the modular tibial stem component 372 comprises a superior stem component piece or segment 374, a first medial stem component piece or segment 376, a second medial stem component piece or segment 378, and an inferior stem component piece or segment 380. The stem component pieces or segments range from 14-18 mm in diameter with a typical 4-piece construct measuring 50 mm in length. This is completely customizable per individual patient need. This segmented design allows for a less invasive approach in prosthetic placement, and more robust anchoring; however, the robust anchoring of the stem pieces or segments into the bone of a distal tibia 304 makes removal of the modular tibial stem component 372 problematic.

Each of the modular stem component pieces or segments 374, 376, 378, and 380 includes a respective external circumferential groove 375, 377, 379, and 381 which may be faceted and which runs along the entire inferior exterior edge of the side of each of the modular stem component pieces or segments 374, 376, 378, and 380.

The modular stem component pieces or segments 374, 376, 378, and 380 each have a specific height and diameter, and different sizes can be combined together to construct the final tibial stem component or tibial prosthetic stem 372.

FIG. 6 exemplifies a blind bore 450 that is disposed through an inferior surface 452 of each tibial stem component piece or segment 374, 376, 378, and 380. Each blind bore 450 includes internal threads 454. Each blind bore 450 has an internal diameter that is configured and sized to receive the outer diameter of a superior threaded protuberance 456 that extends out of a superior surface 458 of each stem component piece and includes external threads 460 that are complemental to the internal threads 454 in the bore 450 of each stem component piece or segment 374, 376, 378, and 380. This allows the modular stem component pieces or segments 374, 376, 378, and 380 to be screwed together to form the final tibial stem component or tibial prosthetic stem 372.

FIG. 7 exemplifies a recessed pattern 470 disposed in the superior surface or closed end of the blind bore 454. In one embodiment, the recessed pattern 470 has a female cruciate slot pattern or shape.

System 3010

Referring again to FIG. 1, an embodiment of the tibial prosthesis removal system 3010 is comprised of a double fork cage 260, a tibial tray alignment insert 3020, a tuning forked shaped adaptor 630, a C-shaped outrigger alignment guide 600, a drill bit guide 234, a drill bit 418, a drill 420, a skeleton cage 240, a bone cutting means 3060, a long handle instrument 3190, a long handle insert 3230, and a central grasping device 3250.

Now referring to FIG. 8, an embodiment of the tibial prosthesis removal system 3010 is further comprised of a tibial prosthesis removal process 3310 for removing the in situ tibial or intramedullary stem component 372 of the total ankle prosthesis 370.

Channel 3012 Formation

Referring to FIGS. 8 and 9, and back to FIG. 1, an embodiment of the tibial prosthesis removal method 3310 comprises a step 3312 of utilizing the double fork cage 260, the tibial tray insert 3020, the tuning forked shaped adaptor 630, the C-shaped outrigger alignment guide 600, the drill bit guide 234, the drill bit 418, and the drill 420 for making a channel 3012 in the calcaneus 360 and talus 330 of a patient that has the in situ tibial or intramedullary stem component 372 that is to be removed.

Double Fork Cage 260

FIG. 10 illustrates one embodiment of the double fork cage or first internal frame 260 of the tibial prosthesis removal system 3010. In this embodiment, the double fork cage 260 is comprised of an anterior frame 262 having three members outlining three sides of a trapezoid. Specifically, the anterior frame 262 is comprised of a superior base member 264 rigidly connected between superior ends of two spaced apart, non-parallel frame members 266, 268. The anterior frame 262 is substantially the size of a tibial-talar space 342 as illustrated in FIG. 11.

Additionally, the double fork frame 260 is comprised of four spaced apart, generally parallel tines 270, 272, 274, and 276 that are operatively coupled to and extend posteriorly off the anterior frame 262 into the superior medial, the superior lateral, the inferior medial, and the inferior lateral edges of the tibial-talar space 342. Anterior frame 262 is comprised of an external handle 278 that extends off an anterior face of one of three members 264, 266, or 268 to aid in manipulating the double fork frame 260 into and out of position. FIG. 10 illustrates the operative connection of the external handle 278 to the frame member 266. The double fork frame 260 is further comprised of two perforated tabs 280, 282 that can be used to connect the frame 260 to the tibia 300 via wires or screws 284 as illustrated in FIG. 11.

In one embodiment, double fork frame 260 is made out of, but not limited to, a metal material or polyethylene.

Tibial Tray Alignment Insert 3020

Body 3022

FIG. 12 illustrates one embodiment of the tibial tray alignment insert 3020 of the tibial prosthesis removal system 3010. In this embodiment, the alignment insert 3020 comprises a generally pyramidal frustum shaped or trapezoidally shaped alignment insert body 3022 that is designed to fit into the tibial-talar space 342 (FIG. 14) defined as the space between the tibia 300 and the talus 330 after the talar dome component 388 and the talar stem component 390 have been removed, and the polyethylene or poly insert component 384 has been removed from the tibial tray component 382 of the in situ tibial prosthesis 396. The tibial tray alignment insert 3020 corresponds to the size of the chosen prosthesis 370 to be removed, so if there are five different prosthesis sizes to choose from then there are five different tibial tray alignment insert sizes for providing a one to one correspondence between the two.

Referring to FIGS. 12 and 13, the alignment insert body 3022 is comprised of six faces: a superior face 3024, an inferior face 3026, an inner face 3028, an outer face 3030, a posterior face 3032, and an anterior face 3034. The superior face 3024 and the inferior face 3026 have a generally square or rectangular shape while the inner face 3028, outer face 3030, posterior face 3032, and anterior face 3034 have a generally trapezoidal shape.

Superior Grooves 3036, 3038

Additionally, and referring to FIG. 12, the alignment insert body 3022 is comprised a pair of generally parallel and spaced apart notched and recessed patterns forming a pair of generally parallel and spaced apart superior grooves 3036 and 3038. Superior groove 3036 is defined as the first superior groove 3036 that extends along the superior longitudinal edge of inner face 3028 and superior groove 3038 is defined as the second superior groove 3038 that extends along the superior longitudinal edge of outer face 3030. This groove pattern corresponds to the pair of the spaced apart trackways or inwardly tapered side rails 440 disposed on the underside or inferior surface 442 of the tibial tray 382 of the in situ tibial prosthesis 396 such that the first and second superior grooves 3036, 3038 are able to respectively slide on the spaced apart trackways or side rails 440 of the tibial tray 382 after the poly insert component 384 has been removed.

Detent 3040

Furthermore, and referring to FIG. 12, an embodiment of the alignment insert body 3022 is further comprised of an upwardly projecting protrusion or detent 3040 near a superior edge of the anterior face 3034.

Referring now to FIGS. 12 and 14, the protrusion or detent 3040 is sized and configured to rest within the notch 446 disposed in the underside 442 of the tibial tray component 382.

In one embodiment, the upwardly projecting protrusion or detent 3040 (FIG. 12) briefly rides against the underside 442 of the tibial tray component 382 and then fits into the notch 446 thereof when the first and second superior grooves 3036, 3038 are respectively slid onto the spaced apart trackways or inwardly tapered side rails 440 of the tibial tray component 382 while the stop flange 448 along the posterior edge of the tibial tray component 382 precludes over-travel of the tibial tray alignment insert 3020 in a posterior direction by engaging with the posterior face 3032 of the alignment insert body 3022 in an abutting relation.

The abutment of the posterior face 3032 and the stop flange 448 is sized and configured to occur in concert with the snap-fit engagement of the protrusion or detent 3040 within the notch 446 disposed in the underside 442 of the tibial tray component 382 for positioning the tibial tray alignment insert 3020 into the tibial-talar space 342 as illustrated in FIG. 15.

Figure 16:
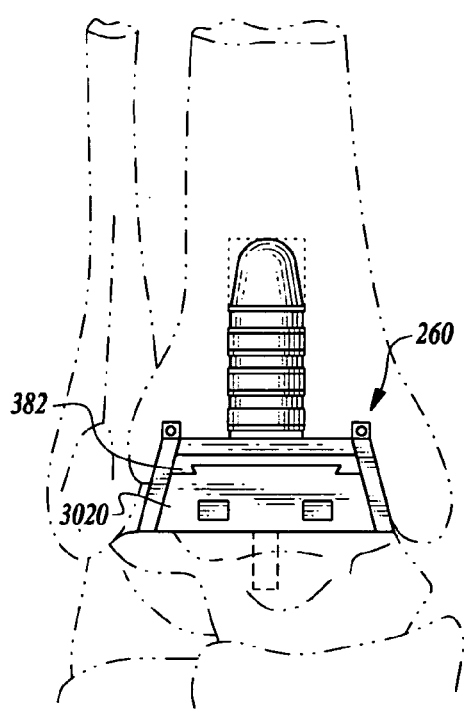
FIG. 16 is a front elevational view of the in situ tibial prosthesis, the double fork frame, and the tibial tray alignment insert, and a fragmentary front elevational view of the human leg and foot.

Referring now to FIG. 16 and in one embodiment of use and operation, the double fork cage 260 is placed in the tibial-talar space 342 (FIG. 14).

Then, the tibial tray alignment insert 3020 is passed through a central anterior open portion 286 (FIG. 10) of the double fork cage 260 and coupled to the inferior tibial tray component 382 as described herein.

The double fork cage 260 and the tibial tray alignment insert 3020 remain therein until the channel 3012 is formed as delineated hereinbelow.

Attachment Channels 3042, 3044

Figure 17:
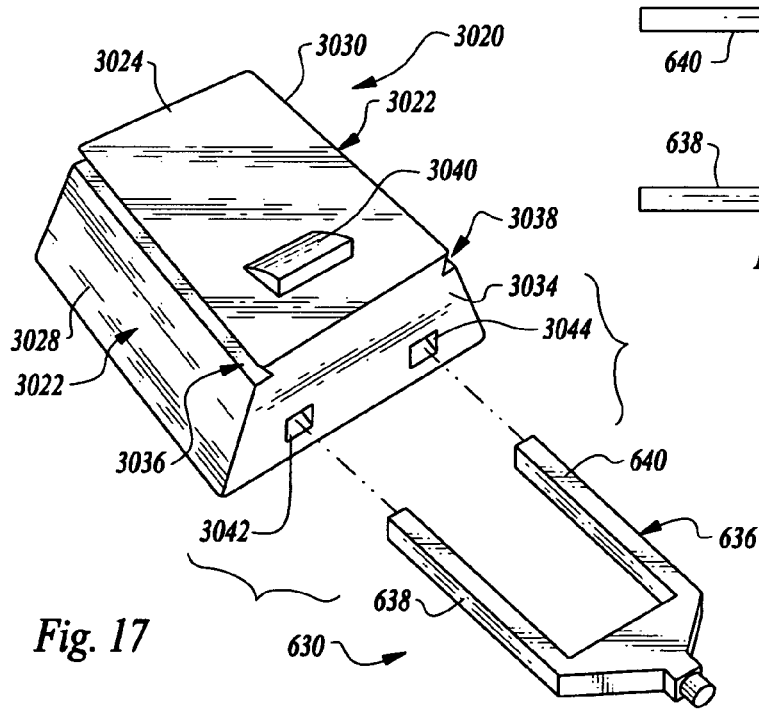
FIG. 17 is a side, front, and top perspective view of the tibial tray alignment insert and the tuning fork shaped adaptor illustrated in FIG. 9.

Referring now to FIG. 17, the alignment insert body 3022 of the tibial tray alignment insert 3020 is further comprised of two attachment channels 3042, 3044 for respectively receiving a pair of spaced apart furcations or tines 638, 640 of a forked end portion 636 of a tuning forked shaped adapter 630. The two attachment channels 3042, 3044 pass from the anterior surface 3034 of the alignment insert body 3022 and may pass through the entire body 3022 or partially therethrough to a depth that accommodates, but that is limited to, the full length of the tines 638, 640 of the tuning forked shaped adapter 630.

Additionally, a width of separation between the channels 3042, 3044 corresponds to the width of separation between the tines 638, 640 on the corresponding tuning fork adapter 630 as illustrated in FIG. 17.

In one embodiment, the tibial tray alignment insert 3020 is made out of, but not limited to, a metal material or polyethylene, and is constructed as, but not limited to, an integrally formed one piece insert.

Tuning Fork Shaped Adaptor 630

Figure 19:
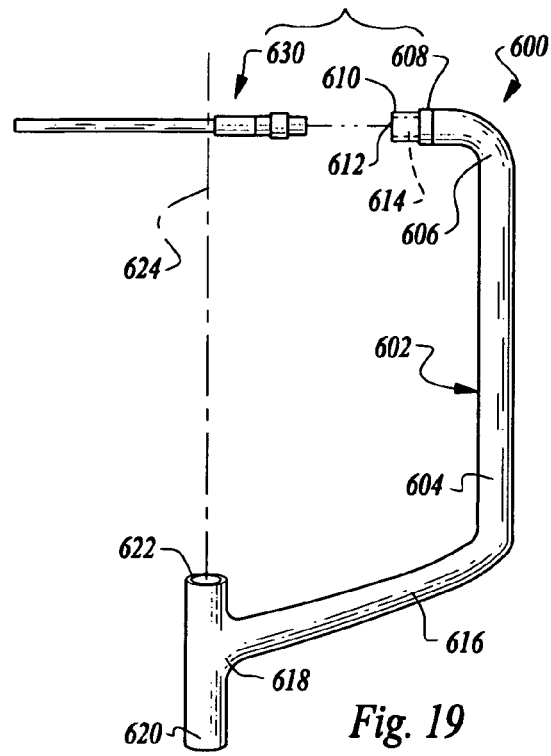
FIG. 19 is a side elevational view of the tuning fork shaped adaptor and the C-shaped outrigger alignment guide illustrated in FIG. 9.
Figure 18:
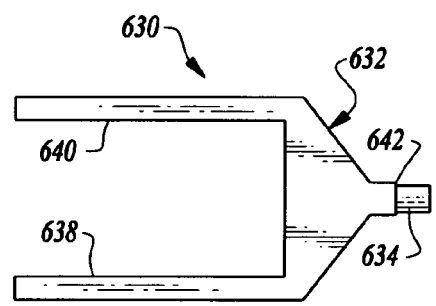
FIG. 18 is a top elevational view of the tuning fork shaped adaptor.

Referring now to FIGS. 17 through 19, and more particularly, the tuning forked shaped adapter 630 is comprised of a body 632 having a friction fitting end portion 634 sized and shaped to be received and frictionally fit within a blind bore 614 of a friction fitting end 610 of the C-shaped outrigger alignment guide 600 as further delineated below.

Additionally, the body 632 of the tuning forked shaped adapter 630 includes an opposing forked end portion 636 comprised of the spaced apart furcations or tines 638, 640 having a specific length for attaching or coupling to the alignment insert body 3022 of the tibial tray alignment insert 3020 as delineated above.

The tuning fork shaped adapter 630 further comprises a stop portion 642 disposed at a distal end of the friction fitting end portion 634 of adaptor 630 for abutting against a front face of a circumscribing wall 612 of the friction fitting end 610 of the C-shaped outrigger alignment guide 600 for precisely locating the tuning fork shaped adapter 630 onto the C-shaped outrigger alignment guide 600 as further delineated below.

In one embodiment, a specifically sized tuning fork shaped adapter 630 can be provided for each different size of each tibial tray alignment insert 3020 for each different size of chosen prosthesis 370. Accordingly, a specific size of the tuning fork shaped adapter 630 can be provided for each specific size of the tibial tray alignment insert 3020 such that for each matching set a width between the tines on the adaptor matches a width between corresponding channels of the tibial tray alignment insert. The length of the tines can also be specific to each matching set.

Additionally, and in one embodiment, each tuning fork shaped adapter is made out of, but not limited to, a metal material or polyethylene, and is constructed as, but not limited to, an integrally formed one piece adapter.

C-Shaped Outrigger Alignment Guide 600

Referring to FIG. 19, the C-shaped outrigger alignment guide 600 is comprised of an arcuate or generally C-shaped body 602 comprised of a medial section 604 transitioning at one end to a superior section 606 and at the other end to an inferior section 616.

The superior section 606 generally perpendicularly extends away from the medial section 604 in substantially the same plane as the medial section 604, and then arches or bends out of the plane of the medial section 604 and transitions to the superior end or head 608 supporting a friction fitting 610. In one embodiment, the friction fitting 610 circumferentially steps down from and is integrally formed with the superior end 608. The friction fitting end 610 is comprised of the posteriorly extending wall 612 circumscribing an interior surface defining the blind bore 614. As noted above, the blind bore 614 is sized to receive and frictionally fit with the complementally shaped end 634 (FIG. 18) of the tuning forked shaped adaptor 630 which, in turn, is received by the tibial tray alignment insert 3020 as delineated above for aligning the C-shaped outrigger alignment guide 600 in a stable position relative to a central long axis 398 (FIG. 11) of the in situ tibial prosthesis 396 and, in particular, the in situ tibial or intramedullary stem component 372 that is to be removed as will be further delineated below.

The inferior section 616 generally perpendicularly extends away from the medial section 604 in substantially the same plane as the medial section 604, and then arches or bends out of the plane of the medial section 604 and transitions to an inferior end 618 supporting an inferior cylindrically shaped inferior sleeve attachment or distal sleeve 620 having an open ended cylindrically shaped bore 622 axially extending therethrough and having a central axis 624.

The distal sleeve 620 is integrally formed with and extends from both sides of the inferior end 618, and is spaced from and generally parallel with the medial section 604.

The open ended cylindrically shaped bore 622 of the distal sleeve 620 is sized to closely receive the inner drill and driver bit guide 234 having open ended cylindrically shaped interior bore 236 extending therethrough (FIG. 21). The open ended cylindrically shaped interior bore 236 of the drill and driver bit guide 234 is sized to closely receive and pass the drill bit 418 therethrough.

In an alternative embodiment, the open ended cylindrically shaped bore 622 of the distal sleeve 620 is sized to closely receive and pass the drill bit 418 therethrough without utilizing the drill and driver bit guide 234.

In one embodiment, the C-shaped outrigger alignment guide 600 is made out of, but not limited to, a metal or polyethylene material and is constructed as, but not limited to, an integrally formed one piece guide.

Additionally, and in one embodiment, the drill bit 418 and guide 234 are made out of, but not limited to a metal or polyethylene material.

Furthermore, and in another embodiment, the tuning-fork adaptor 630 and the C-shaped outrigger alignment guide 600 may be integrally formed together as one piece instrument.

Moreover, and in a further embodiment, the tuning-fork adaptor 630, the C-shaped outrigger alignment guide 600, and the tibial tray alignment insert 3020 may be integrally formed together as one piece instrument.

Insert 3020, Adaptor 630, and Guide 600 Coupling Configuration

Referring to FIG. 20, and in one embodiment, the central long axis 398 of the in situ tibial or intramedullary stem component 372 of the total ankle prosthesis 370 will align or be coincident with the axis 624 of the distal sleeve 620 of the C-shaped outrigger alignment guide 600 when the posterior face 3032 of the tibial tray alignment insert 3020 abuts against the stop flange 448 of the in situ tibial tray component 382, the tines 638, 640 of the tuning fork shaped adapter 630 are fitted into the respective channels 3042, 3044 disposed in the tibial tray alignment insert 3020 (FIG. 17) until the anterior surface 3034 of the tibial tray alignment insert 3020 is completely seated against the body 632 (FIG. 18) of the tuning fork shaped adapter 630, and the friction fitting 634 of the tuning fork shaped adapter 630 is engaged with the friction fitting end 610 (FIG. 19) of the C-shaped outrigger alignment guide 600 until the stop portion 642 of adaptor 630 abuts against front face of circumscribing wall 612 of the friction fitting end 610 of the C-shaped outrigger alignment guide 600 thereby making the axis 624 of the distal sleeve 620 of the C-shaped outrigger alignment guide 600 coextensive with the central long axis 398 of the in situ tibial or intramedullary stem component 372 as illustrated in FIG. 20.

Drill Bit Guide 234, Drill Bit 418, and Drill 420

Referring to FIG. 21, and as discussed above, the open ended cylindrically shaped bore 622 of the distal sleeve 620 is sized to closely receive the inner sleeve drill and driver bit guide 234 having open ended cylindrically shaped interior bore 236 extending therethrough. The open ended cylindrically shaped interior bore 236 of the drill and driver bit guide 234 is sized to closely receive and pass a drill bit 418 therethrough.

In an alternative embodiment, the inner sleeve drill and driver bit guide 234 is eliminated and the open ended cylindrically shaped bore 622 of the distal sleeve 620 is sized to closely receive and pass the drill bit 418 therethrough.

In one embodiment, the drill bit has a diameter of at least six millimeters (6 mm).

Channel 3012

As illustrated in FIGS. 20 and 21, the central axis 624 of the inferior sleeve attachment or drill guide 620 is aligned with the central long axis 398 of the in situ tibial stem component 372. With this alignment, an incision is formed on the bottom of the heel at a location on the heel that is axially aligned with the central axis 624 of the inferior sleeve attachment 620 of the C-shaped outrigger alignment guide 600.

Figures 22, 23:
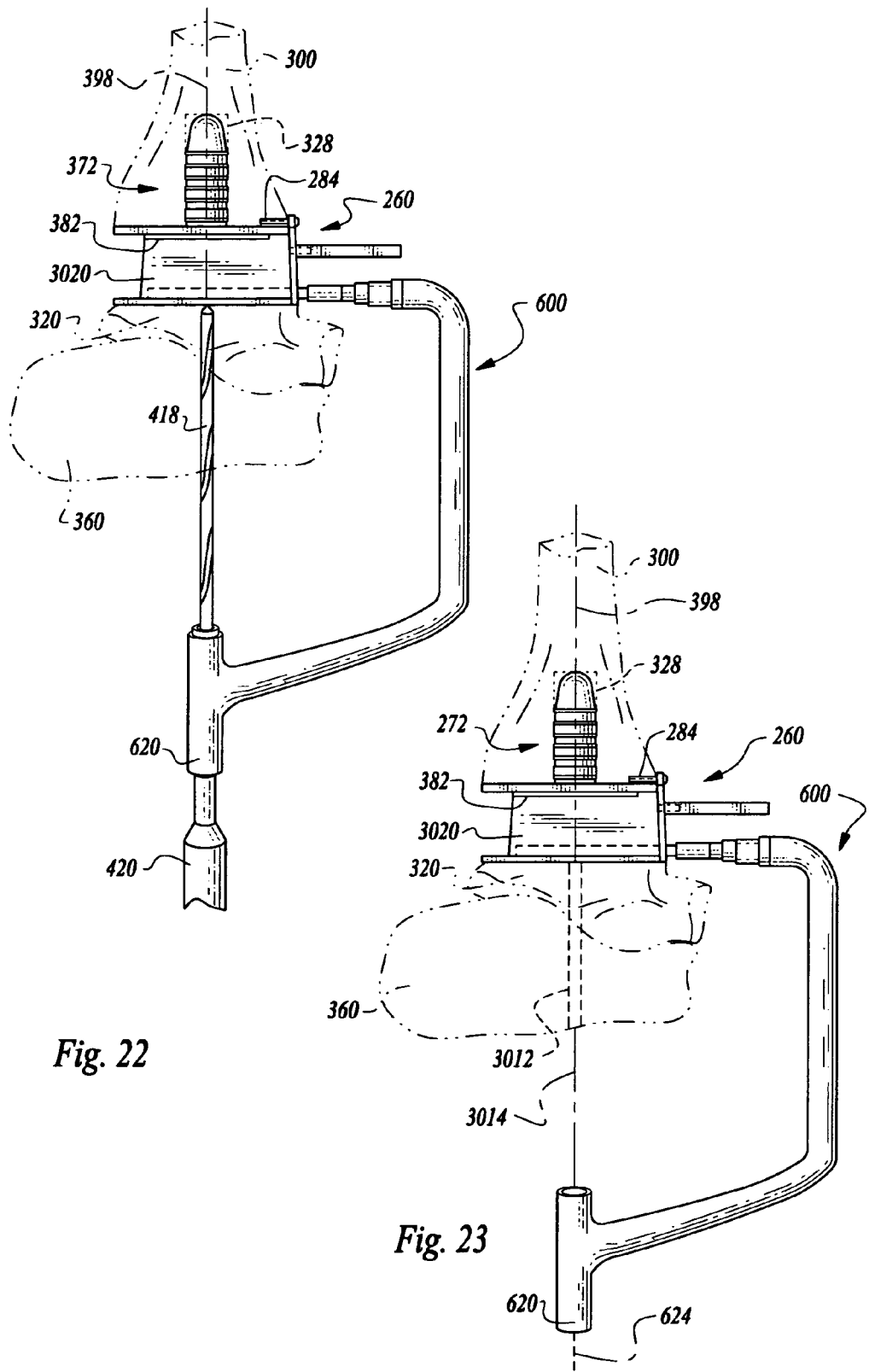
FIG. 22 is a side elevational view of the double fork frame in the tibial-talar space, the tibial tray alignment insert operatively coupled to the tibial tray, the C-shaped outrigger alignment guide operatively coupled to the tibial tray alignment insert through the tuning fork shaped adaptor, the drill guide received within an inferior sleeve attachment of the C-shaped outrigger alignment guide and the conventional surgical drill shown fragmented and operatively coupled to the drill bit that has been drilled up through the bottom of the calcaneus and the talus, and up to the tibial tray alignment insert along a central long axis of the modular tibial stem component of the in situ tibial prosthesis even if even the modular tibial stem component implant has shifted into a slight angulation off the alignment of the original insertion axis.
FIG. 23 is a side elevational view of the channel formed in the calcaneus and talus with the instrumentalities illustrated in FIG. 22 with the drill bit and drill removed and with the C-shaped outrigger alignment guide, the tuning fork shaped adaptor, the tibial tray alignment insert, the double fork frame, and the in situ tibial prosthesis remaining.

Then, the drill guide 234 is placed in the inferior sleeve attachment 620 and the drill bit 418 having, in one embodiment, at least a 6 mm diameter is driven by drill 420 up through the calcaneus 360 and talus 330 bones as illustrated in FIG. 22, forming or creating the channel 3012 through bones 360, 330 that comprises a channel axis 3014 that is substantially coincident or coextensive with the central long axis 398 of the in situ tibial stem component 372 as illustrated in FIG. 23.

After the channel 2012 is formed, the drill bit 418 is removed from the channel 2012.

Next, the drill guide 234 is removed from the inferior sleeve attachment 620 of C-shaped outrigger alignment guide 600.

This is followed by the sequential removal of the C-shaped outrigger alignment guide 600, the tuning fork shaped adapter 630, and the tibial tray alignment insert 3020.

Then, the inferior tibial tray component 382 is decoupled from the inferior stem piece 380 of the chosen prosthesis 370 and removed.

After the inferior tibial tray component 382 removed, the double fork cage or first internal frame 260 is then removed as described below.

Ankle Stabilization

Referring again to the flowchart of FIG. 8, and with channel 3012 formed, an embodiment of the tibial prosthesis removal process 3310 comprises a step 3314 of utilizing the skeleton cage 240 for stabilizing at least the ankle of the patient having the in situ tibial or intramedullary stem component 372 that is to be removed.

The skeleton cage 240 is configured to fit snugly in the space between the tibia 300 and talus 330 defined as the tibial-talar space 342.

Skeleton Cage 240

With the inferior tibial tray component 382 removed, the double fork cage or first internal frame 260 can be removed and replaced with the skeleton cage 240.

Referring now to FIGS. 24 and 25, and as noted above, an embodiment of the tibial prosthesis removal system 3010 is comprised of the skeleton cage 240 which replaces the double fork cage 260. The skeleton cage 240 is comprised of a posterior transverse member 242 rigidly connected between two superior portions of two spaced apart, rectangularly shaped, and inwardly slanting frames 244, 246 for providing the skeleton cage 240 with an external shape that is generally congruent with the generally pyramidal frustum shape of the tibial tray alignment insert 3020 so as to fit snugly in the space between the tibia 300 and talus 330 defined as the tibial-talar space 342 as illustrated in FIG. 25.

In one embodiment, the skeleton cage 240 has an external handle 248 operatively connected to and extending from an anterior edge of at least one of frame members 244, 246 to aid in manipulating the skeleton cage 240 into and out of the tibial-talar space 342. FIGS. 24 and 25 illustrate the operative coupling of the external handle 248 to the outer frame member 244.

A central anterior open portion 250 of the skeleton cage or frame 240 allows the stem pieces 380, 378, 376, and 374 of the modular tibial stem component 372 to be sequentially accessed, worked upon as delineated in further detail below, and easily passed through skeleton cage 240 and out of the tibial-talar space 342 after removal from the tibia 300.

Additionally, the skeleton cage 240 is comprised of two perforated tabs 252, 254 that can be used to connect the skeleton cage 240 to the tibia via wires or screws 256 as illustrated in FIG. 25.

In one embodiment, each skeleton cage is made out of, but not limited to, a metal material or polyethylene.

Circumferentially Cutting Tibia Circumscribing Inferior Most Stem Piece

Referring again to FIG. 8, and with channel 3012 formed and the ankle is stabilized with the skeleton cage 240, an embodiment of the tibial prosthesis removal process 3310 comprises a step 3316 of circumferentially cutting the tibia bone circumscribing an inferior most stem piece of the in situ tibial or intramedullary stem component 372 for forming a circumscribing tibia bone cut around the inferior most stem piece.

Offset Chisel 3070

Referring now to FIG. 26, an embodiment of the bone cutting means 3060 is in the form of, but not limited to, an offset chisel device 3070 having a central longitudinal axis 3072. The offset chisel device 3070 is comprised of an elongated shaft 3074 and a chisel head portion 3082. The elongated shaft 3074 is sized and configured to pass through the channel 3012 formed in the calcaneus 360 and talus 330 and up through the tibial-talar space 342. In one embodiment, the elongated shaft 3074 is cylindrically shaped with a diameter that slideably fits within channel 3012. Additionally, the elongated shaft 3074 comprises a threaded proximal end 3076 that is sized to pass through channel 3012 and an opposing distal end 3078 that, in one embodiment, terminates to a handle 3080 for grasping.

FIG. 27 illustrates the chisel head portion 3082 of the offset chisel device 3070. The chisel head portion 3082 is comprised of a hollow annular base 3084 having a central threaded interior surface 3086 defining a central opening for the threaded proximal end 3076 of the elongated shaft 3074 to pass into and threadedly couple therewith such that the central longitudinal axis of the shaft is coincident with a central longitudinal axis of the hollow annular base 3084. Offset from the opening of the hollow annular base 3084 is a chisel 3088. The chisel 3088 includes an offset portion 3090 upwardly and outwardly diverging from the exterior surface of the hollow annular base 3084 and a cutting portion or blade 3092 upwardly transitioning away from the offset portion 3090 in a direction that is parallel with the central longitudinal axis 3072 of the offset chisel device 3070 or, in other words, the central longitudinal axis of the hollow annular base 3084 and elongated shaft 3074. The cutting portion or blade 3092 of the chisel 3088 is formed with at least a superior sharp edge 3094 and has a radius of curvature 3096 that matches the radius of curvature of the most inferior tibial stem piece as illustrated in FIG. 28.

Figure 29:
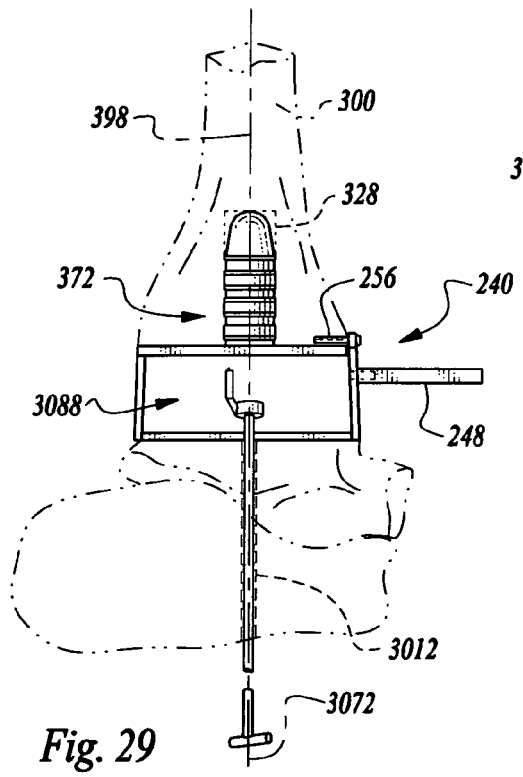
FIG. 29 is a side elevational view of the skeleton cage or frame positioned in the tibial-talar space, a side elevational view of the modular tibial stem component, and a side elevational view of the offset chisel device having its elongated shaft passing through the channel and in alignment with the tibial stem component such that the central axis of the elongated shaft and the tibial stem component are coincident or coextensive with respect to one another, and further illustrating a fragmented view of the tibia, talus, and calcaneus.

As also illustrated in FIG. 29, the offset portion 3090 is such that the central longitudinal axis 3072 of the offset chisel device 3070 and the central long axis 398 of the in situ tibial or intramedullary stem component 372 are coextensive or coincident with one another. In this configuration, the chisel 3088 should then just pass beyond the vertical surface of the most inferior tibial stem piece and be configured to have a length that just passes beyond the vertical surface of the body of the most inferior tibial stem piece. Accordingly, the offset chisel device 3070 that is used at any given time is sized in accordance with the size of the most inferior tibial stem piece that is currently being removed.

The offset chisel device 3070 is designed to be assembled by passing the elongated shaft 3074 through the channel 3012 and then have the chisel head portion 3082 placed into the tibial-talar space 342 from the anterior incision and central anterior open portion 250 (FIG. 24) of the skeleton cage or frame 240. The threaded proximal end 3076 of the elongated shaft 3074 then engages the central threaded interior surface 3086 of the hollow annular base 3084 of the chisel head portion 3082. The offset chisel device 3070 is then reciprocated to free any bone around the sides of the inferior most stem piece of the in situ tibial or intramedullary stem component 372 that is to be removed. Preferably, the height of the cutting portion or blade 3092 is approximately the height of the inferior most stem piece of the in situ tibial or intramedullary stem component 372. It cannot be substantially larger, because it must be small enough to fit into the tibial-talar space 342.

In one embodiment, each offset chisel device is made out of, but not limited to, a metal material.

Cylindrical Saw Device 3100

Figure 30:
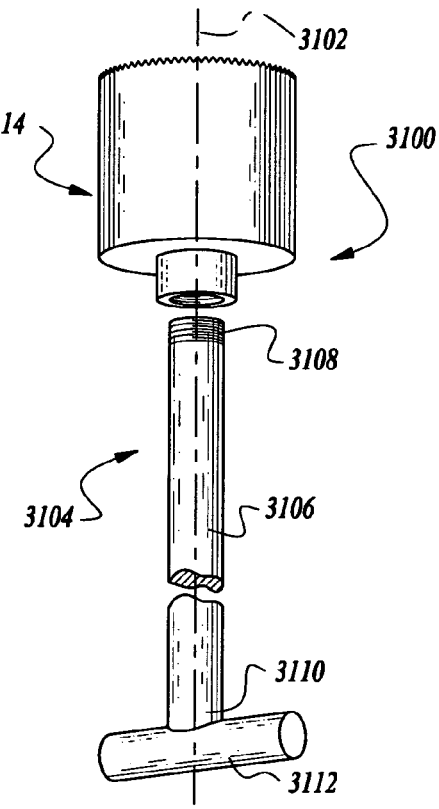
FIG. 30 is an exploded parts view of a bone cutting means in the form of an embodiment of a long handle cylindrical saw device comprised of a cylindrical saw driver and a cylindrical saw head.

Referring now to FIG. 30, and in another embodiment, the bone cutting means 3060 is in the form of, but not limited to, a cylindrical saw device 3100 having a central longitudinal axis 3102. The cylindrical saw device 3100 is comprised a cylindrical saw head 3114 detachably coupled to a cylindrical saw driver 3104.

Cylindrical Saw Driver 3104

The cylindrical saw driver 3104 is comprised of an elongated shaft 3106 sized and configured to pass through the channel 3012 formed in the calcaneus 360 and talus 330 and up through the tibial-talar space 342.

In one embodiment, the elongated shaft 3106 is cylindrically shaped with a diameter that slideably fits within channel 3012.

Additionally, the elongated shaft 3106 comprises a threaded proximal end 3108 that is sized to pass through channel 3012 and an opposing distal end 3110 that, in one embodiment, terminates to a handle 3112 for grasping and rotating the cylindrical saw device 3100.

In one embodiment, the cylindrical saw driver 3104 is made out of, but not limited to, a metal material.

Cylindrical Saw Head 3114

As noted above, and referring to FIG. 31, the cylindrical saw device 3100 is further comprised of the cylindrical saw head 3114. The cylindrical saw head 3114 comprises an inferior circular base 3116 having an outer circumscribing periphery 3117 transitioning into a cylindrically shaped side wall 3118 arising from the inferior circular base 3116 forming a shell of a cylinder and defining an internal cylindrically shaped cavity 3120. The cylindrically shaped side wall 3118 terminates to superior circular cutting edge or cutting rim 3122.

There are different sizes of the cylindrical saw head 3114 corresponding to the different sizes of the modular stem component pieces or segments 374, 376, 378, and 380 of modular tibial stem component 372. The chosen saw diameter and depth should allow the most inferior tibial stem component piece that is being removed to fit within the cavity 3120 of the cylindrical saw head 3114. Thus, for each modular stem component piece or segment, the internal diameter of the cylindrical saw head 3114 or the diameter of cavity 3120, should be just greater than the diameter of the most inferior tibial stem component piece being removed, and the internal depth of the cylindrical saw head 3114 or cavity 3120 minus the height of an interior portion of an interior protruding member 3124 should be just greater than the height of the most inferior tibial stem component piece being removed.

Preferably, the cylindrical saw had 3114 has a very thin cylindrically shaped side wall for ensuring that the kerf of the circumscribing bone cut from the sides of the most inferior tibial stem component is minimal during removal of the most inferior tibial stem component piece or segment.

Figure 31:
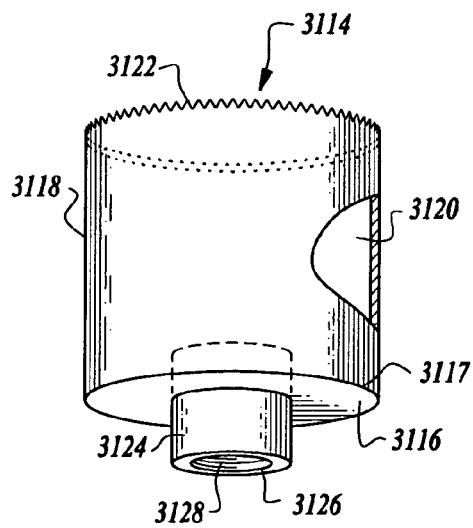
FIG. 31 is a side perspective view of the cylindrical saw head illustrated in FIG. 30 with a portion cut away to illustrate an internal cavity thereof.

Still referring to FIG. 31, the cylindrical saw head 3114 further comprises the hollow cylindrically shaped protruding member 3124 extending superiorly and inferiorly from the surfaces of the circular base 3116. The protruding member 3124 comprises a circular opening 3126 extending therethrough and defined by a central threaded interior surface 3128 having threads complemental to the threaded proximal end 3108 of the cylindrical saw driver 3104 for threadedly coupling thereto.

In one embodiment, the cylindrical saw head 3114 is made out of, but not limited to, a metal material.

Figure 32:
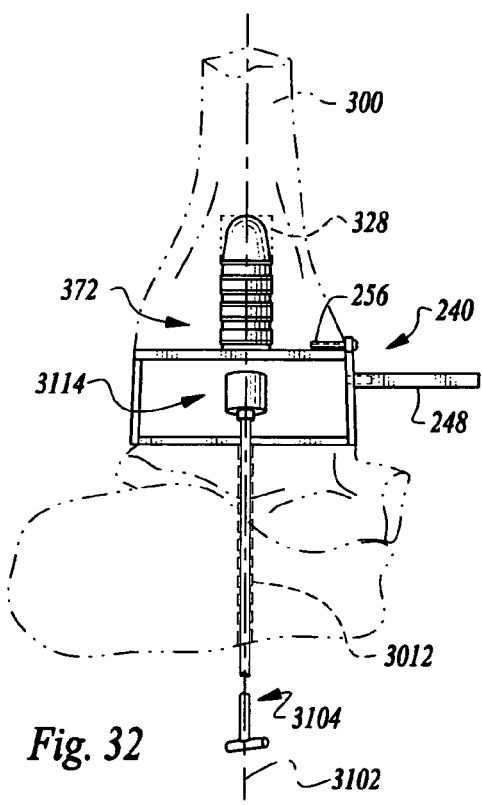
FIG. 32 is a side elevational view of the skeleton cage positioned in the tibial-talar space, the in situ modular tibial stem component, and the long handle cylindrical saw device having an elongated shaft of the cylindrical saw driver passing through the channel and engaged with the cylindrical saw head in the tibial-talar space such that that the central axis of the elongated shaft, the cylindrical saw head, and in situ modular tibial stem component are coincident or coextensive with respect to one another, and further illustrating a fragmented view of the tibia, talus, and calcaneus.

Referring now to FIGS. 30 through 32, the cylindrical saw device 3100 is designed to be assembled by passing the elongated shaft 3106 of the cylindrical saw driver 3104 through the channel 3012 and into the tibial-talar space 342 (FIG. 25) and then have the cylindrical saw head 3114 placed into this space from the anterior incision and central anterior open portion 250 (FIG. 24) of the skeleton cage or frame 240. The threaded proximal end 3108 of the elongated shaft 3106 then engages the central threaded interior surface 3128 of the protruding member 3124 of the cylindrical saw head 3114. The cylindrical saw device 3100 is put into place over the most inferior tibial stem component piece or segment being removed and rotated for cutting a circumscribing cut around and adjacent to the exterior circumscribing side surface of the most inferior tibial stem component piece or segment of the in situ tibial or intramedullary stem component 372 that is to be removed.

In another embodiment, the cylindrical saw driver 3104 is devoid of the handle 3112 adjacent distal end 3110 such that the distal end 3110 can be operatively coupled to and driven by drill 420 (FIG. 21) for rotating cylindrical saw head 3114 for cutting a circumscribing cut around and adjacent to the exterior circumscribing side surface of the most inferior tibial stem component piece or segment of the in situ tibial or intramedullary stem component 372 that is to be removed.

Cylindrical Saw and Threaded Centering Device 3130

Referring now to FIG. 33, and in another embodiment, the bone cutting means 3060 is in the form of, but not limited to, a cylindrical saw and threaded centering device 3130 having a central longitudinal axis 3132. The cylindrical saw and threaded centering device 3130 is comprised of a cylindrical saw head 3134, a cylindrical saw driver 3154, and a centering device 3170.

Cylindrical Saw Head 3134

The cylindrical saw head 3134 comprises an inferior circular base 3136 having an outer circumscribing periphery transitioning into a cylindrically shaped side wall 3138 arising from the inferior circular base 3136 forming a shell of the cylindrical saw head 3134 and defining an internal cylindrically shaped cavity or socket 3140. The cylindrically shaped side wall 3138 terminates to a superior circular cutting edge or cutting rim 3142.

The cylindrical saw head 3134 further comprises a hollow cylindrically shaped interior protruding member 3144 extending superiorly from the inferior circular base 3136 and an exterior protruding member 3146 extending inferiorly from the inferior circular base 3136 and axially aligned with the interior protruding member 3144. The exterior protruding member 3146 having a centrally located and axially elongated slot 3148 disposed therein.

Additionally, the axially aligned interior and exterior protruding members 3144 and 3146, and the inferior circular base 3136, comprise a central circular opening or bore 3150 extending therethrough. The central circular opening or bore 3150 is parallel to the cylindrically shaped side wall 3138 and perpendicular to the inferior circular base 3136.

Furthermore, the central axis of the central circular opening 3150 is axially aligned or coincident with the central longitudinal axis 3132 of the cylindrical saw and threaded centering device 3130.

Analogous to the cylindrical saw head 3114, the cylindrical saw head 3134 is provided in different sizes corresponding to the different sizes of the modular stem component pieces or segments 374, 376, 378, and 380 of modular tibial stem component 372.

The chosen saw diameter and depth should allow the most inferior tibial stem component piece that is being removed to fit within the cavity or socket 3140 of the cylindrical saw head 3134.

Thus, for each modular stem component piece or segment, the internal diameter of the cylindrical saw head 3134 or the diameter of cavity 3140, should be just greater than the diameter of the most inferior tibial stem component piece being removed, and the internal depth of the cylindrical saw head 3114 or cavity 3140 minus the height of the interior protruding member 3144 should be just greater than the height of the most inferior tibial stem component piece being removed.

Furthermore, the cylindrical saw head 3134 has a very thin cylindrically shaped side wall for ensuring that the kerf of the circumscribing bone cut from the sides of the most inferior tibial stem component is minimal during removal of the most inferior tibial stem component piece or segment.

In one embodiment, the cylindrical saw head 3134 is made out of, but not limited to, a metal material.

Cylindrical Saw Driver 3154

Still referring to FIG. 33, and as noted above, the cylindrical saw and threaded centering device 3130 is further comprised of the cylindrical saw driver 3154. The cylindrical saw driver 3154 is comprised of a cylindrically shaped elongated shaft 3156 sized and configured to pass through the channel 3012 formed in the calcaneus 360 and talus 330 and up through the tibial-talar space 342. In one embodiment, the elongated shaft 3156 is cylindrically shaped with a diameter that slideably fits within channel 3012. Additionally, the elongated shaft 3156 comprises a proximal end 3158 that transitions into a tab or key head 3160. Opposing the proximal end 3158 is a distal end 3162 of the elongated shaft 3156. The elongated shaft 3156 is hollow with a bore 3164 extending therethrough. The bore 3164 has a diameter substantially equal to the diameter of the circular opening 3150 of the cylindrical saw head 3134 and has a longitudinal axis that is centrally located along the central long axis of the elongated shaft 3156.

As illustrated in FIG. 33, the central axis of the elongated shaft 3156 and thus, the hollow bore 3164, is axially aligned or coincident with the central longitudinal axis 3132 of the cylindrical saw and threaded centering device 3130.

In one embodiment, the distal end 3162 of the elongated shaft 3156 is operatively coupled to and driven by drill 420 for rotating the cylindrical saw head 3134 while the threaded centering device 3170 remains stationary.

In one embodiment, the cylindrical saw driver 3154 is made out of, but not limited to, a metal material.

Threaded Centering Device 3130

Still referring to FIG. 33, and as noted above, the cylindrical saw and threaded centering device 3130 is further comprised of the threaded centering device 3170. The threaded centering device 3170 comprises an elongated pin shaft 3172 having a diameter that is just less than both the diameter of the central circular opening 3150 of the cylindrical saw head 3134 and the diameter of the central bore 3164 of the cylindrical saw driver 3154 for being closely received therein as further delineated below. The elongated pin shaft 3172 of the threaded centering device 3170 includes a lower or distal end 3174 and an opposing upper or proximal end 3176.

In one embodiment, the length of the elongated pin shaft 3172 is such that it is just greater than the distance between the inferior or lowermost surface of the exterior protruding member 3146 and the superior or uppermost surface of the cutting edge or cutting rim 3142 of the cylindrical saw head 3134.

The threaded centering device 3170 is further comprised of a threaded head 3178 centered and mounted on the upper or proximal end 3176 of the elongated pin shaft 3172. The threaded head 3178 includes an inferior surface having a patterned recess or notch 3180 disposed therein. In one embodiment, the patterned recess 3180 is in the form of a female cruciate slot pattern or configuration.

In one embodiment, the threaded centering device 3170 is made out of, but not limited to, a metal material or polyethylene.

Long Handle Instrument 3190

Referring now to FIG. 34, and as noted above, the tibial prosthesis removal system 3010 is further comprised of the long handle instrument 3190. The long handle instrument 3190 is comprised of a cylindrically shaped elongated shaft 3192 sized and configured to pass through the channel 3012 formed in the calcaneus 360 and talus 320 and up through the tibial-talar space 342.

Additionally, the elongated shaft 3192 comprises a proximal end 3194 that transitions into a male patterned blade or head 3196 that is complemental to patterned recess 3180. In one embodiment, the male patterned blade 3196 is in the form of a male cruciate pattern or configuration complemental to the female cruciate slot pattern or configuration of one embodiment of the patterned recess 3180 for receipt thereby. Opposing the proximal end 3194 is a distal end 3198 of the elongated shaft 3192. The distal end 3198 transitions into a handle 3200 of the elongated shaft 3192.

Furthermore, the elongated shaft 3192 is hollow with a bore 3202 extending therethrough along a central long axis 3204 of the elongated shaft 3192. The bore 3202 has a diameter just greater than the diameter of the elongated pin shaft 3172 of the threaded centering device 3170 such that the elongated pin shaft 3172 can be received therein as illustrated in FIG. 35.

More specifically, and referring to FIGS. 35 and 36, the long handle instrument 3190 is configured to pass through the channel, receive the elongated pin shaft 3172 into its bore 3202, and engage with the threaded centering device 3170 by way of an abutment between the male patterned blade 3196 of the long handle instrument 3190 and the patterned recess 3180 of the threaded centering device 3170. After the abutment is made, the long handle instrument 3190 is rotated clockwise to screw the threaded centering device 3170 into the inferior threaded bore of the most inferiorly located tibial stem component piece and then, the long handle instrument 3190 is disengaged from the threaded centering device 3170 as illustrated in FIG. 36.

Figure 37:
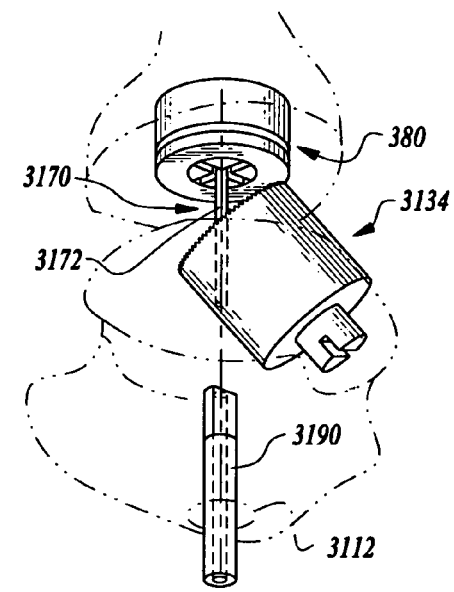
FIG. 37 is a side elevational view of an elongated shaft of the cylindrical saw driver which is illustrated in FIG. 33 and which is passing through the channel and terminating to a tab end in the tibial-talar space, and a side elevational view of the cylindrical saw head illustrated in a tilted position for receiving an elongated pin shaft of the threaded centering device threadedly engaged with the most inferiorly located tibial stem component piece for passing the elongated pin shaft through a central circular opening of the cylindrical saw head and a central bore extending through the cylindrical saw driver.

Referring to FIGS. 33 and 37, the cylindrical saw and threaded centering device 3130 is designed to be assembled by passing the elongated shaft 3156 of the cylindrical saw driver 3154 through the channel 3012 and into the tibial-talar space 342 and then tilting and placing the cylindrical saw head 3134 into this space from the anterior incision and central anterior open portion 250 of the skeleton cage or frame 240. With the cylindrical saw head 3134 tilted, the elongated pin shaft 3172 is passed into the cavity 3140 of the cylindrical saw head 3134. Then, cylindrical saw head 3134 is up righted and the elongated pin shaft 3172 is aligned with and passed through the circular opening 3150. Next, the key head 3160 of the elongated shaft 3156 is mated with slot 3148 of the cylindrical saw head 3134 with the elongated pin shaft 3172 being received within the hollow bore 3164 of the elongated shaft 3156 of the cylinder saw driver 3154 operatively coupled to drill 420 to be driven thereby.

Figure 38:
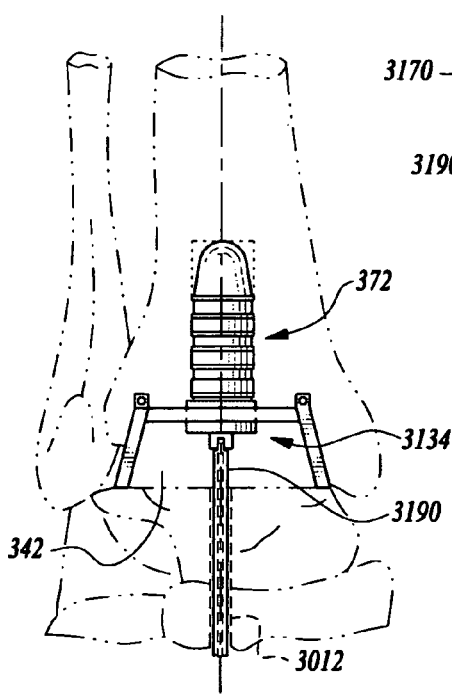
FIG. 38 is a front elevational view of the elongated shaft of the cylindrical saw driver of the cylindrical saw and threaded centering device passing through the channel with the tab engaged in a slot of the cylindrical saw head which is circumscribing the most inferiorly located tibial stem component piece threadedly engaged with the centering device having its elongated pin shaft passing through the central circular opening of the cylindrical saw head and into the central bore of the cylindrical saw driver wherein the central axis of the cylindrical saw driver, the cylindrical saw head, and the threaded centering device is coextensive or coincident with the central long axis of the most inferiorly located tibial stem component piece for forming a circumscribing kerf around the most inferiorly located tibial stem component piece by rotationally driving the cylindrical saw driver.

As illustrated in FIG. 38, the cylindrical saw head 3134 is put into place over the most inferior tibial stem component piece or segment being removed and rotated by drill 420 for cutting a circumscribing cut around and adjacent to the exterior circumscribing side surface of the most inferior tibial stem component piece or segment of the in situ tibial or intramedullary stem component 372 that is to be removed.

Figure 39:
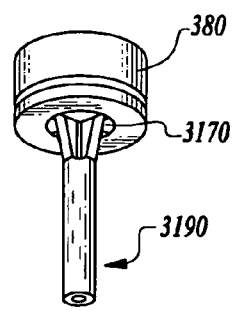
FIGS. 39 and 40 are side elevational views depicting the removal of the threaded centering device from the most inferiorly located tibial stem component piece utilizing the long handle instrument illustrated in FIG. 34.
Figure 40:
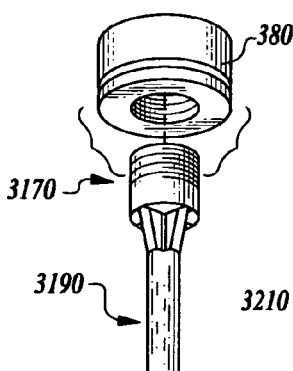

With the circumscribing cut accomplished and the cylindrical saw driver 3154 and cylindrical saw head 3134 removed, the cylindrically shaped elongated shaft 3192 of the long handle instrument 3190 is again passed up through the channel 3012 to remove the threaded centering device 3170 in a manner opposite to its insertion as described above and illustrated in FIGS. 39 and 40.

In one embodiment, the long handle instrument 3190 is made out of, but not limited to, a metal material.

Cylindrical Saw and Patterned Centering Device 3210

Figure 41:
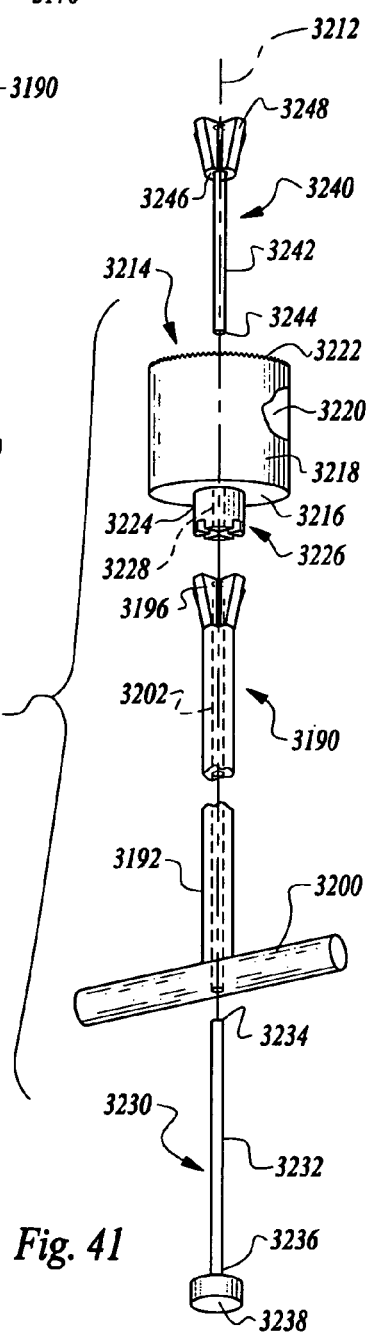
FIG. 41 is an exploded parts view of an embodiment of a combination cylindrical saw and patterned centering device.
Figure 42:
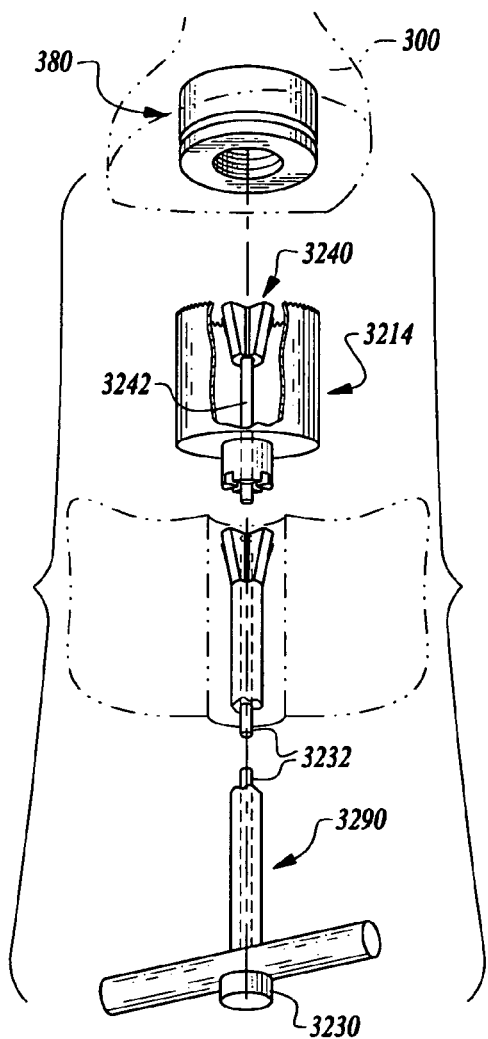
FIG. 42 is a side elevational view of the elongated shaft of the long handle instrument passing through the channel and terminating to the patterned head in the tibial-talar space, and a side elevational view of a cylindrical saw head (illustrated in FIG. 41) receiving an elongated pin shaft of a patterned centering device (illustrated in FIG. 41) through an inferior opening and into a central bore of the long handle instrument via a superior opening thereof, and the long handle insert having an embodiment of an elongated pin shaft received into the central bore of the long handle instrument by way of an inferior opening thereof, and further illustrating the most inferiorly located tibial stem component and a fragmented view of the tibia, talus, and calcaneus.

Referring now to FIGS. 41 and 42, and in another embodiment, the bone cutting means 3060 is in the form of, but not limited to, a cylindrical saw and patterned centering device 3210 having a central longitudinal axis 3212. The cylindrical saw and threaded centering device 3210 is comprised of a cylindrical saw head 3214, a cylindrical saw driver taking the form of the long handle instrument 3190, a long handle insert 3230, and a patterned head centering device 3240.

Cylindrical Saw Head 3214

Referring to FIG. 41, the cylindrical saw head 3214 comprises an inferior circular base 3216 having an outer circumscribing periphery transitioning into a cylindrically shaped side wall 3218 arising from the inferior circular base 3216 forming a shell of the cylindrical saw head 3214 and defining an internal cylindrically shaped cavity or socket 3220. The cylindrically shaped side wall 3218 terminates to a superior circular cutting edge or cutting rim 3222.

The cylindrical saw head 3214 further comprises a hollow cylindrically shaped protruding member 3224 extending superiorly and inferiorly from the inferior circular base 3216. The protruding member 3224 includes an inferior surface having a patterned recess or notch 3226 disposed therein. In one embodiment, the patterned recess 3226 is in the form of a female cruciate slot pattern or configuration.

Additionally, the protruding member 3224 and the inferior circular base 3216 comprise a central circular opening or bore 3228 extending therethrough. The central circular opening or bore 3228 is parallel to the cylindrically shaped side wall 3218 and perpendicular to the inferior circular base 3216. Furthermore, the central axis of the central circular opening 3228 is axially aligned or coincident with the central longitudinal axis 3212 of the cylindrical saw and patterned centering device 3210.

Analogous to the cylindrical saw heads 3114 and 3134, the cylindrical saw head 3214 is provided in different sizes corresponding to the different sizes of the modular stem component pieces or segments 374, 376, 378, and 380 of modular tibial stem component 372.

The chosen saw diameter and depth should allow the most inferior tibial stem component piece that is being removed to fit within the cavity or socket 3220 of the cylindrical saw head 3214 as delineated with respect to cylindrical saw heads 3114 and 3134.

Furthermore, the cylindrical saw head 3214 has a very thin cylindrically shaped side wall for ensuring that the kerf of the circumscribing bone cut from the sides of the most inferior tibial stem component is minimal during removal of the most inferior tibial stem component piece or segment.

In one embodiment, the cylindrical saw head 3214 is made out of, but not limited to, a metal material.

Cylindrical Saw Driver/Long Handle Instrument 3190

Referring to FIGS. 34 and 41, and as noted above, the cylindrical saw and patterned centering device 3210 is further comprised of a cylindrical saw driver which takes the form of the long handle instrument 3190 which has been described in detail hereinabove and which is illustrated in FIG. 34.

Long Handle Insert 3230

Referring to FIG. 41, and as noted above, the cylindrical saw and patterned centering device 3210 is further comprised of the long handle insert 3230. In one embodiment, the long handle insert 3230 is comprised of a pin like cylindrical shaft 3232 sized with a diameter that can be received through the inferior opening of the central bore 3202 of the long handle instrument 3190 and with a length that just exceeds the length of the long handle instrument 3190 so that insert 3230 can pass through the superior opening of the central bore 3202 of the long handle instrument 3190. The cylindrical shaft 3232 includes a superior end 3234 and an opposing inferior end 3236 that transitions into a knob 3238 centered on the shaft 3232 and that allows the long handle insert to be grasped by fingers.

In one embodiment the long handle insert 3230 is made out of, but not limited to, a metal material.

Threaded Centering Device 3130

Referring to FIG. 41, and as noted above, the cylindrical saw and patterned centering device 3210 is further comprised of the patterned head centering device 3240.

The patterned head centering device 3240 comprises an elongated pin shaft 3242 having a diameter that is just less than both the diameter of the central circular opening 3228 of the cylindrical saw head 3214 and the diameter of the central bore 3202 of the long handle instrument 3190 for being closely received therein. In one embodiment, the length of the elongated pin shaft 3242 is such that it is just greater than the cylindrical saw head 3214.

The patterned head centering device 3240 is further comprised of a patterned head 3248 centered and mounted on the upper or proximal end 3246 of the elongated pin shaft 3242. In one embodiment, the patterned head 3248 is in the form of a male cruciate slot pattern or configuration complementally shaped to be received by the recessed pattern 462 of the inferior most tibial stem component piece or segment of the in situ tibial or intramedullary stem component 372 that is to be removed.

Referring to FIG. 42, the use of the cylindrical saw and patterned centering device 3210 generally follows that of the cylindrical saw and threaded centering device 3130. Specifically, the cylindrical saw and patterned centering device 3210 is designed to be assembled by passing the elongated shaft 3192 of the long handle instrument 3190 through the channel 3012 and into the tibial-talar space 342 and then tilting and placing the cylindrical saw head 3214 into this space from the anterior incision and central anterior open portion 250 of the skeleton cage or frame 240. With the cylindrical saw head 3214 tilted, the elongated pin shaft 3242 is passed into the central circular opening 3228 of the cylindrical saw head 3214. Then, cylindrical saw head 3214 is up righted and the elongated pin shaft 3242 is aligned with and passed through the circular opening 3228. Next, the male patterned blade 3196 of the long handle instrument 3190 is mated with the patterned recess 3226 of the cylindrical saw head 3214 while the elongated pin shaft 3242 is received within the hollow bore 3202 of the elongated shaft 3192 of the long handle instrument 3190 via a superior opening of the hollow bore 3202. Then, the superior end 3234 is received within the hollow bore 3202 of the elongated shaft 3192 of the long handle instrument 3190 via an inferior opening of the hollow bore 3202 and is pushed superiorly until abutting against the elongated pin shaft 3242 of the patterned head centering device 3240. In this configuration, and with the knob 3238 of the long handle insert 3230 pressed up against the handle 3200 of the long handle instrument 3190, the handle 3200 is utilized to place the cylindrical saw head 3214 in place over the most inferior tibial stem component piece or segment being removed and is rotated by for cutting a circumscribing cut around and adjacent to the exterior circumscribing side surface of the most inferior tibial stem component piece or segment of the in situ tibial or intramedullary stem component 372 that is to be removed.

Unscrewing Inferior Most Tibial Stem Component Piece

Referring again to FIG. 8, and with the circumscribing cut accomplished and the embodiment of the bone cutting means 3060 removed, an embodiment of the tibial prosthesis removal process 3310 comprises a step 3318 of unscrewing the most inferior tibial stem component piece or segment of the in situ tibial or intramedullary stem component 372 utilizing the aligned channel 3012.

Figure 43:
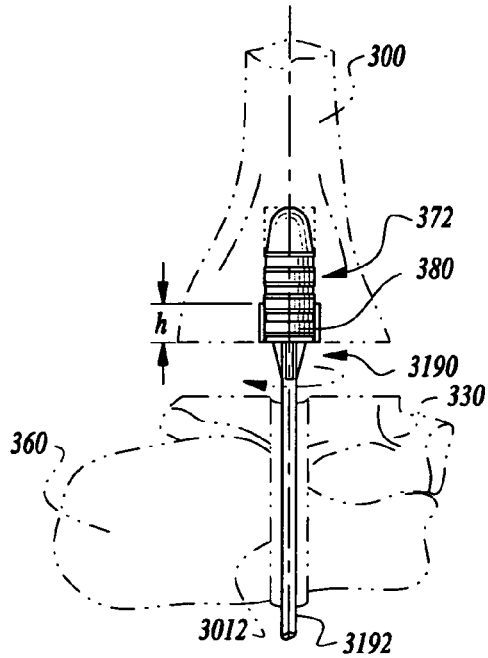
FIGS. 43 and 44 are side elevational views depicting the unscrewing of the most inferiorly located tibial stem component piece from the inferiorly penultimate tibial stem component piece utilizing the long handle instrument illustrated in FIG. 34 after a circumscribing kerf has been formed around the most inferiorly located tibial stem component piece.
Figure 44:
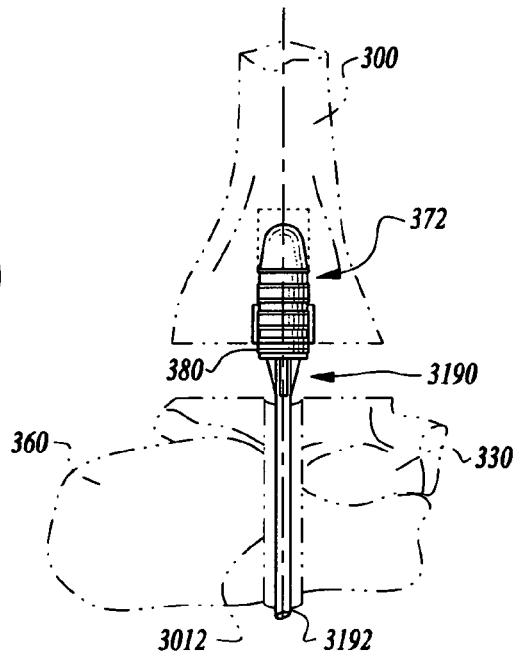

Referring to FIGS. 43 and 44, and in one embodiment, the cylindrically shaped elongated shaft 3192 of the long handle instrument 3190 is again passed up through the aligned channel 3012 to unscrew the most inferior tibial stem component piece or segment of the in situ tibial or intramedullary stem component 372 as illustrated.

Grasping and Removing Inferior Most Tibial Stem Component Piece

Referring again to FIG. 8, and with the most inferior tibial stem component piece or segment of the in situ tibial or intramedullary stem component 372 unscrewed, an embodiment of the tibial prosthesis removal process 3310 comprises a step 3318 of grasping and removing the unscrewed inferior most tibial stem component piece or segment of the in situ tibial or intramedullary stem component 372 by utilizing the aligned channel 3012.

Central Grasping Device 3280

Referring to FIGS. 45 through 50, and as noted above, the tibial prosthesis removal system 3010 is comprised of a grasping means in the form of the central grasping device 3250 which is utilized as necessary to grasp, remove, and perhaps further unscrew the unscrewed inferior most tibial stem component piece or segment of the in situ tibial or intramedullary stem component 372 by utilizing the aligned channel 3012.

Figure 45:
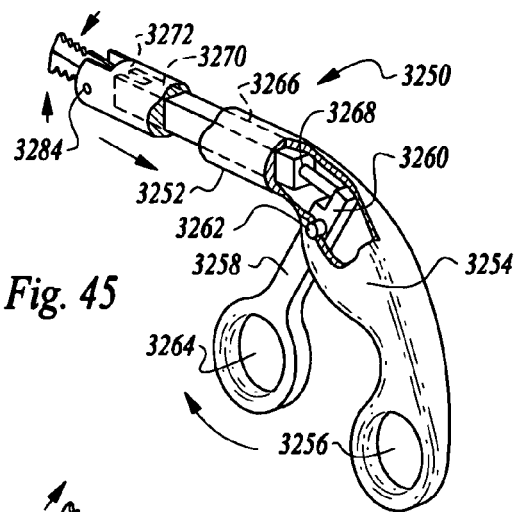
FIG. 45 is a side perspective view of an embodiment of a central grasping device having a pair of jaws illustrated in an inwardly closed position.

Referring to FIG. 45, the central grasping device 3250 is comprised of an elongated chamber member 3252 having a longitudinal axis, an open distal end, and an open proximal end which transitions into a support handle 3254 terminating in an inferior finger loop 3256. Additionally, the central grasping device 3250 comprises a pivot handle 3258 having a superior end 3260 pivotally coupled to the support handle 3254 via handle pivot pin 3262 at a location proximate the open proximal end of the elongated chamber member 3252. Furthermore, the pivot handle 3258 comprises an inferior finger loop 3264. Moreover, the central grasping device 3250 comprises an actuator 3266 slideably disposed within the elongated chamber member 3252. Actuator 3266 includes a proximal end 3268 connected to the superior end 3260 of the pivot handle 3258 and a distal end 3270 having a groove 3272 disposed therein.

Figure 46:
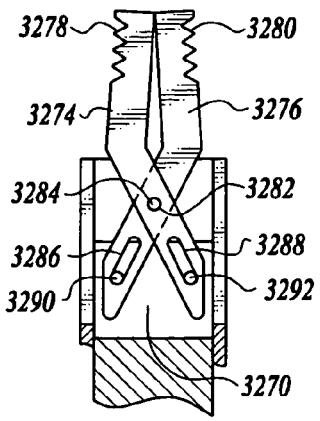
FIG. 46 is a fragmented view of the central grasping device further detailing the pair of jaws in the inwardly closed position.

Referring to FIG. 46, the central grasping device 3250 further comprises two tines 3274, 3276 that are mirror images of each other. On a distal end of each of the two tines 3274, 3276 are respective outwardly facing grooves or threads 3278, 3280 that preferably correspond to the internal threads 454 of the bore 450 of each of the modular stem component pieces or segments 374, 376, 378, and 380. Adjacent a medial portion of each of the two tines 3274, 3276 is an elongated hole 3282 passing through the two tines 3274, 3276 with a fixed pin 3284 closely fitted therein so that the two tines 3274, 3276 can pivot thereabout. Adjacent a proximal portion of tine 3274 is an elongated hole 3288 passing through the tine 3274 with a fixed pin 3292 closely fitted therein to provide a slidable coupling between the actuator 3266 and the tine 3274 at a location within the groove 3272 of the actuator 3266. Adjacent a proximal portion of tine 3276 is an elongated hole 3286 passing through the tine 3276 with a fixed pin 3290 closely fitted therein to provide a slidable coupling between the actuator 3266 and the tine 3276 at a location within the groove 3272 of the actuator 3266.

Figure 49:
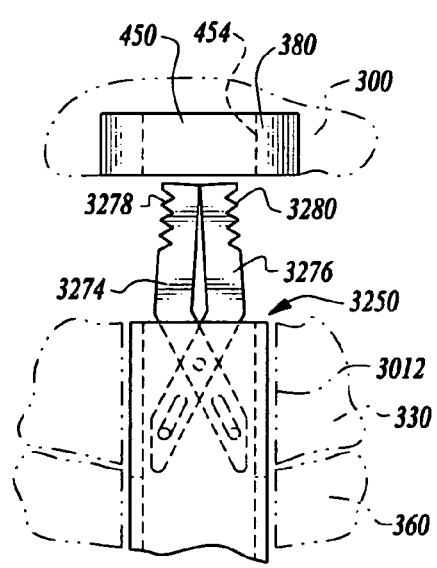
FIG. 49 is a side elevational view of an elongated shaft of the central grasping device passing through the channel and terminating to the pair of jaws in the inwardly closed position in the tibial-talar space.

Accordingly, when the pivot handle 3258 is in an unactuated state or position as illustrated in FIGS. 45, 46, and 49 the two tines 3274, 3276 are brought together as illustrated in FIG. 46. When the two tines 3274, 3276 are brought together, the distance between the outer surfaces of the threads must be less than the internal diameter of the bore in the most inferior tibial stem piece as illustrated in FIG. 49.

Figure 47:
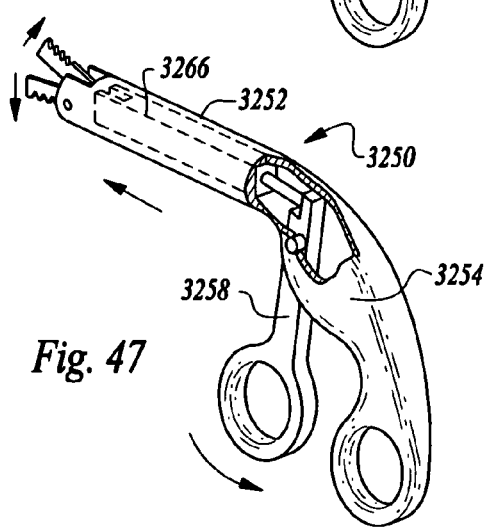
FIG. 47 is a side perspective view of the central grasping device having a pair of jaws illustrated in an outwardly open position.
Figure 48:
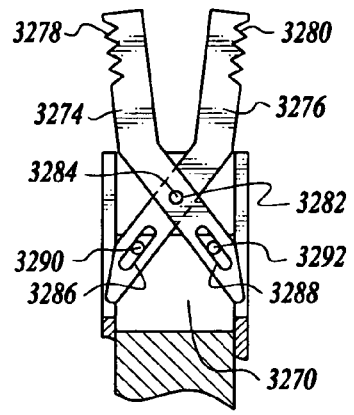
FIG. 48 is a fragmented view of the central grasping device further detailing the pair of jaws in the outwardly open position.
Figure 50:
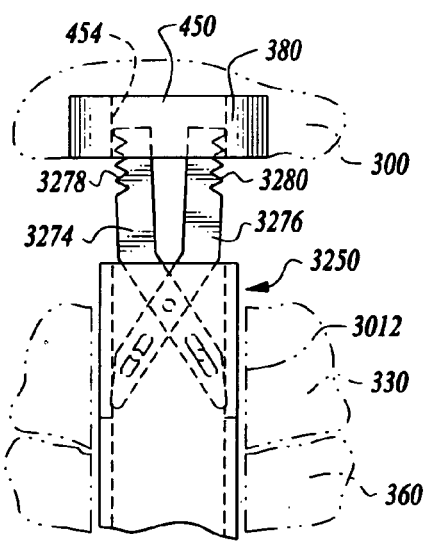
FIG. 50 is a side elevational view of the elongated shaft of the central grasping device passing through the channel and terminating to the pair of jaws which are passing into an inferior bore of a loose or unscrewed tibial stem component piece and which are in the outwardly open position for grasping the loose or unscrewed tibial stem component piece and positioning it into the tibial-talar space for removal therefrom.

Conversely, when the pivot handle 3258 is squeezed toward the support handle 3254, the actuator 3266 slides forward within the elongated chamber member 3252 and the two tines 3274, 3276 slideably coupled thereto are separated as illustrated in FIGS. 47, 48, and 50 with the outwardly facing grooves or threads 3278, 3280 radially outwardly separating from one another and with the proximate ends thereof being allowed to separate apart because of the groove 3272 of the actuator 3266. Thus, as the handles 3254, 3258 are squeezed together, the actuator 3266 gets pushed distally thereby spreading the two tines 3274, 3276 apart and as the handles 3254, 3258 are pulled apart, the actuator 3266 pulled back causing the two tines 3274, 3276 to come together.

In one embodiment, the central grasping device 3250 is formed from, but not limited to, a metal material. Additionally, an embodiment of the elongated chamber member 3252 has an outer diameter that is less than six millimeters.

Referring to FIG. 49, the elongated chamber member 3252 is passed through the aligned channel 3012 with the tines 3274, 3276 together. Still together, the tines 3274, 3276 are located within the threaded blind bore 450 of the most inferior tibial stem component piece or segment of the in situ tibial or intramedullary stem component 372. Next, and as illustrated in FIG. 50, the handles 3254, 3258 are squeezed together thereby spreading the outwardly facing grooves or threads 3278, 3280 of the two tines 3274, 3276 into engagement with the threads 454 of the threaded blind bore 450 of the most inferior tibial stem component piece or segment of the in situ tibial or intramedullary stem component 372. With the handles 3254, 3258 squeezed together and the outwardly facing grooves or threads 3278, 3280 of the two tines 3274, 3276 engaged with the threads 454 of the threaded blind bore 450, the most inferior tibial stem component piece or segment of the in situ tibial or intramedullary stem component 372 is grasped and can be further unscrewed if necessary and pulled down into the tibial-talar space 342 for removal.

Removing Remaining Tibial Stem Component Pieces or Segments

Referring again to FIG. 8, the tibial prosthesis removal process 3310 comprises a step 3322 of deciding if further tibial stem component pieces or segments remain implanted. If further tibial stem component pieces or segments do not remain implanted, then the process 3310 ends at step 3324. If further tibial stem component pieces or segments do remain implanted, then the process 3310 loops back to step 3316 and repeats steps 3316, 3318, and 3320 until all of the tibial stem component pieces or segments have been removed.

In Use and Operation

In use and operation, and referring to the drawings, an embodiment of the tibial prosthesis removal system 3010 is illustrated for removing an embodiment of a tibial prosthesis having an intramedullary stem 372 comprised of a plurality of modular tibial stem component pieces disposed in a tibial blind bore 328. Following an anterior ankle skin incision, the polyethylene insert component 384, the talar dome component 388, and the talar stem component 390 are removed from the in situ total ankle prosthesis 370 while the modular tibial stem component 372 comprised of a plurality of stem component pieces and the tibial tray component 382 remain in situ as illustrated in FIG. 14.

With these components removed, a method of use and operation of the system 3010 for removing the modular tibial stem component 372 comprises a step of forming a channel 3012 through the talus 330 and the calcaneus 360 that is substantially axially aligned with the longitudinal axis 398 of the in situ tibial stem component 372 even if the modular tibial stem component 372 has shifted into a slight angulation off the alignment of the original insertion axis for allowing a series of instruments, as will be delineated herein, to pass through the channel 3012 to aid in removing the plurality of stem pieces of the modular tibial stem component 372. In one embodiment, the channel is substantially about 6 mm in diameter to allow for passage of the series of instruments.

More particularly, and in one embodiment, the channel forming step comprises placing the double fork frame 260 in the tibial-talar space 342 for holding the bones apart and allowing access to the tibial tray component 382.

Then, the channel forming step comprises locating the tibial tray alignment insert 3020 into the tibial tray component 382 by sliding the grooves 3036, 3038 of the tibial tray alignment insert 3020 onto the pair of the spaced apart trackways 440 of the tibial tray 382 such that the grooves slide on the trackways while the upwardly projecting detent member 3040 slides in the channel in an anterior to posterior direction until the detent member 3040 encounters the notch 446 and snap-fits thereto while the stop flange 448 along the posterior edge of the tibial tray 382 precludes over-travel in a posterior direction by engaging with the posterior face 3032 of the tibial tray alignment insert 3020 in an abutting relation. The engagement of the stop flange 448 and posterior face 3032 is sized and configured to occur in concert with the snap-fit engagement of the detent member 3040 within the notch 446.

Then, the channel forming step comprises coupling the tuning fork shaped adaptor 630 to the C-shaped outrigger alignment guide 600 and fitting or coupling the C-shaped outrigger alignment guide 600 to the tibial tray alignment insert 3020 through the tuning fork shaped adaptor 630 wherein this coupling aligns the central axis 624 of the inferior sleeve attachment or drill guide 620 with the longitudinal axis 398 of the in situ tibial stem 372.

Then, the channel forming step comprises making an incision on the bottom of the heel at a location on the heel that is axially aligned with the inferior sleeve attachment 620 of the C-shaped outrigger alignment guide 600.

Next, the channel forming step comprises placing the drill guide 234 in the inferior sleeve attachment 620 and utilizing a drill bit 418 having, in one embodiment, at least a 6 mm diameter for drilling up through the calcaneus 360 and talus 330 bones, forming or creating the channel 3012 through these bones 360, 330 that comprises a channel axis 3014 that is substantially centered along the longitudinal axis 398 of the modular tibial stem component 372.

With the channel 3012 formed, and in one embodiment, the next step of the method of use and operation of the system 3010 comprises removing the drill bit 418 from the drill guide 234 and then removing the drill guide 234, the C-shaped outrigger alignment guide 600, and the tibial tray alignment insert 3020 together or separately.

The next step of the method of use and operation of the system 3010 comprises removing the tibial tray component 382 from the inferior stem piece 380 of the modular tibial stem component 372.

Then, placing the skeleton cage 240 into the tibial-talar space 342 for holding the bones apart for allowing access to the most inferior tibial stem piece.

In one embodiment, the next step of the method of use and operation of the system 3010 comprises utilizing the bone cutting means 3060 as delineated hereinabove for cutting the tibial bone attached to the walls of the most inferior tibial stem piece until the bone has been cut completely away from the most inferior tibial stem piece circumferentially. The next step of the method of use and operation of the system 3010 comprises the removal of the bone cutting means 3060.

Then, passing the long handle instrument 3190 back up through the channel 3012 and into the intramedullary passageway and rotating the long handle instrument 3190 as necessary for abuttingly and complementally engaging the patterned blade mounted on the superior end of the long handle insert with the patterned notch on the blind bore end of the most inferior tibial stem piece 380, 378, 376, or 374. Next, rotating the long handle instrument 3190 for unscrewing the most inferior tibial stem piece from the remaining stem piece above it. Then, removing the long handle instrument 3190 from the intramedullary passageway and channel 3012 and the most inferior tibial stem piece from the tibial-talar space 342. If the stem piece remains in the intramedullary passageway, the next step is comprised of passing the central grasping device upward through the channel in the calcaneus and talus and into the intramedullary passageway for grasping the most the most inferior tibial stem piece as illustrated in FIGS. 49 and 50 and positioning the most inferior tibial stem piece into the tibial-talar space 342 for removal through the anterior skin incision.

In an alternative use, the central grasping device may be employed to grasp the most inferior tibial stem piece that has not been unscrewed and pulling the central grasping device for locating the unscrewed inferior tibial stem piece in the tibial-talar space 342, disengaging the central grasping device from the unscrewed most inferior tibial stem piece, unscrewing the most inferior tibial stem piece, and removing the unscrewed inferior tibial stem piece from the tibial-talar space 342 through the anterior skin incision.

In another alternative use, the central grasping device engages most inferior tibial stem piece before it is unscrewed or after it has been partially unscrewed from the remaining tibial stem 372, and the central grasping device is rotated to unscrew the most inferior tibial stem piece from the remaining tibial stem 372.

The next tibial stem piece in the tibial stem 372 then becomes the most inferior tibial stem piece. It is then treated with the method as above and this method is repeated until all of the tibial stem pieces have been removed.

The above delineation of the system 3010 and its method 3310, and its use and operation, demonstrates the industrial applicability of this invention.

Moreover, it should be apparent that numerous modifications and adaptations may be resorted to without departing from the scope and fair meaning of the instant invention as set forth hereinabove and as described herein below by the claims.

I claim:

1. A tibial prosthesis removal system for removing a tibial prosthesis having an intramedullary stem comprised of a plurality of modular tibial stem component pieces having a longitudinal axis and surmounting a tibial tray component located in a tibial-talar space formed by a resected segment of a distal tibia portion and dome portion of a talus bone surmounting a calcaneus bone, said tibial prosthesis removal system comprising:

a tibial tray alignment insert configured to occupy the tibial-talar space and comprising a superior face configured to operatively couple to the tibial tray component;

an alignment guide member having a superior end and an inferior drill guide end, said alignment guide member configured to locate said inferior drill guide end at a location inferior to the calcaneus bone while having said superior end operatively coupled to said tibial tray alignment insert occupying the tibial-talar space for aligning a longitudinal axis of said inferior drill guide end with the longitudinal axis of the plurality of modular tibial stem pieces wherein a drill bit passed through said drill guide will be in alignment to bore a channel through the calcaneus and talus bones with a central channel axis coincident with the longitudinal axis of the plurality of modular tibial stem component pieces; and wherein said tibial tray alignment insert comprises a body having a pair of spaced apart attachment channels disposed through an anterior surface of said body and at least partially through said body.

2. The tibial prosthesis removal system of claim 1 further comprising a tuning forked shaped adapter having a first end configured to couple with said superior end of said alignment guide and having a pair of spaced apart tines configured to closely fit within said pair of attachment channels of said body of said tibial tray alignment insert to operatively couple said superior end to said tibial tray alignment insert for aligning the longitudinal axis of said inferior drill guide end with the longitudinal axis of the plurality of modular tibial stem pieces.

3. The tibial prosthesis removal system of claim 2 further comprising cutting means for circumferentially cutting bone around at least an inferior most in situ modular tibial stem piece after the tibial tray component is removed from the intramedullary stem comprised of the plurality of modular tibial stem component pieces for defining a circumscribing bone kerf around at least the inferior most in situ modular tibial stem piece.

4. The tibial prosthesis removal system of claim 3 further comprising removing means for removing at least the inferior most in situ modular tibial stem piece circumscribed by the bone kerf.

5. The tibial prosthesis removal system of claim 4 wherein said removing means comprises an elongated shaft surmounted by a patterned head wherein at least a portion of said elongated shaft is configured to pass through the channel and wherein said patterned head is configured to pass through the channel and wherein said patterned head is complementally configured to mate with a pattern disposed in a superior surface surmounting a circumscribing wall defining a blind bore disposed through an inferior surface of at least the inferior most in situ modular tibial stem piece so that a directional rotation of said elongated shaft of said removing means will unscrew at least the inferior most in situ modular tibial stem piece from an inferiorly penultimate in situ modular tibial stem piece threadedly coupled thereto.

6. The tibial prosthesis removal system of claim 5 further comprising grasping means for grasping an unscrewed inferior most in situ modular tibial stem piece and positioning said unscrewed inferior most in situ modular tibial stem piece into the tibial-talar space for removal therefrom.

7. The tibial prosthesis removal system of claim 6 wherein said grasping means comprises a hollow elongated chamber configured to at least partially pass through the channel, said hollow elongated chamber having an open distal end and an open proximal end which transitions into a support handle.

8. The tibial prosthesis removal system of claim 7 wherein said grasping means further comprises an actuator slideably disposed within said elongated chamber, a pivot handle operatively coupled to a proximate end of said actuator and pivotally coupled to said support handle, and a pair of tines pivotally coupled to one another at a medial location and each slideably coupled to said distal end of said actuator at a proximal location wherein each of said pair of tines includes distal portions extending beyond said open distal end of said hollow elongated chamber and wherein said distal portions comprise outwardly facing grooves disposed therein such that said distal portions are spread apart when said pivot handle is pivoted toward said support handle and such that said distal portions come together when said pivot handle is pivoted away from said support handle.

9. The tibial prosthesis removal system of claim 8 wherein said pair of tines is configured to pass through the channel and into the blind bore of at least the inferior most in situ modular tibial stem piece when said pivot handle is pivoted away from said support handle and wherein said pair of tines is configured to engage the circumscribing wall of the blind bore when said pivot handle is pivoted toward said support handle for grasping said unscrewed inferior most in situ modular tibial stem piece and positioning it into the tibial-talar space for removal therefrom.

10. The tibial prosthesis removal system of claim 3 wherein said cutting means comprises a cylindrical saw having an inferior base transitioning into a cylindrical sidewall defining an interior cavity and terminating to an annular cutting surface, said cylindrical saw sized to fit within the tibial-talar space and said interior cavity sized to closely receive at least the inferior most in situ modular tibial stem piece.

11. The tibial prosthesis removal system of claim 10 wherein said cutting means further comprises an elongated shaft configured to at least partially pass through the channel and operatively couple to said inferior base of said cylindrical saw and wherein said shaft is configured to pass a rotation thereof to said cylindrical saw for circumferentially cutting bone around at least the inferior most in situ modular tibial stem piece for defining the circumscribing bone kerf around at least the inferior most in situ modular tibial stem piece.

12. The tibial prosthesis removal system of claim 11 wherein said cutting means further comprises a centering device having an elongated pin shaft surmounted by a centering head wherein said elongated pin shaft is configured to pass through a central opening in an inferior circular base of said cylindrical saw and wherein said centering head is configured to removably couple with the inferior most in situ modular tibial stem piece to locate a central axis of said cylindrical saw coincident with a longitudinal axis of at least the inferior most in situ modular tibial stem piece.

13. The tibial prosthesis removal system of claim 3 wherein said cutting means comprises an offset chisel device.

14. The tibial prosthesis removal system of claim 13 wherein said offset chisel device comprises an elongated shaft having a proximal end configured to pass through the channel.

15. The tibial prosthesis removal system of claim 14 wherein said offset chisel device further comprises a chisel head portion comprised of a base configured to operatively couple to said proximal end of said elongated shaft of said offset chisel device.

16. The tibial prosthesis removal system of claim 15 wherein said chisel head portion includes a chisel having an offset portion upwardly and outwardly diverging from an exterior surface of said base and a cutting portion upwardly transitioning away from said offset portion in a direction that is parallel with said elongated shaft of said offset chisel device.

17. The tibial prosthesis removal system of claim 16 wherein said cutting portion is configured to have a radius of curvature that matches a radius of curvature of the inferior most in situ modular tibial stem piece.

18. A tibial prosthesis removal system for removing a tibial prosthesis having an intramedullary stem comprised of a plurality of modular tibial stem component pieces having a longitudinal axis and surmounting a tibial tray component located in a tibial-talar space formed by a resected segment of a distal tibia portion and dome portion of a talus bone surmounting a calcaneus bone, said tibial prosthesis removal system comprising:
a tibial tray alignment insert configured to occupy the tibial-talar space;
said tibial tray alignment insert comprising a body having a pair of spaced apart superior grooves disposed along superior spaced apart longitudinal edges of said body wherein said superior grooves are configured to operatively couple to the tibial tray component; and
an alignment guide member having a superior end and an inferior drill guide end, said alignment guide member configured to locate said inferior drill guide end at a location inferior to the calcaneus bone while having said superior end operatively coupled to said tibial tray alignment insert occupying the tibial-talar space for aligning a longitudinal axis of said inferior drill guide end with the longitudinal axis of the plurality of modular tibial stem pieces wherein a drill bit passed through said drill guide will be in alignment to bore a channel through the calcaneus and talus bones with a central channel axis coincident with the longitudinal axis of the plurality of modular tibial stem component pieces.

19. A tibial prosthesis removal system for removing a tibial prosthesis having an intramedullary stem comprised of a plurality of modular tibial stem component pieces having a longitudinal axis and surmounting a tibial tray component located in a tibial-talar space formed by a resected segment of a distal tibia portion and dome portion of a talus bone surmounting a calcaneus bone, said tibial prosthesis removal system comprising:
a tibial tray alignment insert configured to occupy the tibial-talar space and comprising a superior face configured to operatively couple to the tibial tray component;
an alignment guide member having a superior end and an inferior drill guide end, said alignment guide member configured to locate said inferior drill guide end at a location inferior to the calcaneus bone while having said superior end operatively coupled to said tibial tray alignment insert occupying the tibial-talar space for aligning a longitudinal axis of said inferior drill guide end with the longitudinal axis of the plurality of modular tibial stem pieces wherein a drill bit passed through said drill guide will be in alignment to bore a channel through the calcaneus and talus bones with a central channel axis coincident with the longitudinal axis of the plurality of modular tibial stem component pieces; and
wherein said tibial tray alignment insert further comprises an upwardly projecting protrusion disposed on said superior surface of said body between superior spaced apart longitudinal edges of said body.

* * * * *